(12) United States Patent
Zoller et al.

(10) Patent No.: US 8,399,476 B2
(45) Date of Patent: Mar. 19, 2013

(54) IMIDAZO[1,2-A]PYRIDINES AND THEIR USE AS PHARMACEUTICALS

(75) Inventors: Gerhard Zoller, Schöneck (DE); Hartmut Strobel, Frankfurt am Main (DE); David William Will, Frankfurt am Main (DE); Paulus Wohlfart, Frankfurt am Main (DE)

(73) Assignee: Sanofi, Paris (FR)

( * ) Notice: Subject to any disclaimer, the term of this patent is extended or adjusted under 35 U.S.C. 154(b) by 720 days.

(21) Appl. No.: 12/548,636

(22) Filed: Aug. 27, 2009

(65) Prior Publication Data
US 2010/0113412 A1 May 6, 2010

Related U.S. Application Data

(63) Continuation of application No. PCT/EP2008/001150, filed on Feb. 15, 2008.

(30) Foreign Application Priority Data

Feb. 28, 2007 (EP) .................................. 07004120

(51) Int. Cl.
*A01N 43/42* (2006.01)
*A61K 31/44* (2006.01)
*C07D 491/02* (2006.01)
*C07D 498/02* (2006.01)

(52) U.S. Cl. ........................................ 514/300; 546/121

(58) Field of Classification Search .................. 546/121; 514/300
See application file for complete search history.

(56) References Cited

U.S. PATENT DOCUMENTS

| | | | | |
|---|---|---|---|---|
| 561,453 | A | * | 6/1896 | Juraszyk .......................... 119/75 |
| 3,133,076 | A | * | 5/1964 | Ferrari ........................... 430/570 |
| 3,234,218 | A | * | 2/1966 | Eichenberger et al. ....... 548/193 |
| 4,767,755 | A | | 8/1988 | George et al. |
| 4,808,594 | A | * | 2/1989 | George et al. ................. 514/300 |
| 5,614,531 | A | | 3/1997 | Juraszyk et al. |
| 2004/0023972 | A1 | | 2/2004 | Sundermann et al. |
| 2005/0239822 | A1 | | 10/2005 | Hennies et al. |
| 2006/0276433 | A1 | | 12/2006 | Kawagoe et al. |

FOREIGN PATENT DOCUMENTS

| | | | |
|---|---|---|---|
| EP | 0267111 | | 5/1988 |
| EP | 0668278 | | 8/1995 |
| EP | 1849465 | | 10/2007 |
| FR | 82860 | * | 4/1964 |
| FR | 2606409 | * | 5/1988 |
| WO | WO 99/47153 | | 9/1999 |
| WO | WO 00/03746 | | 1/2000 |
| WO | WO 02/30428 | | 4/2002 |
| WO | WO 02/064146 | | 8/2002 |
| WO | WO 02/064545 | | 8/2002 |
| WO | WO 02/064546 | | 8/2002 |
| WO | WO 02/064565 | | 8/2002 |
| WO | WO 02/066477 | | 8/2002 |
| WO | WO 02/085903 | | 10/2002 |
| WO | WO 03/000689 | | 1/2003 |
| WO | WO 03/042188 | | 5/2003 |
| WO | WO 2004/014369 | | 2/2004 |
| WO | WO 2004/014372 | | 2/2004 |
| WO | WO 2004/014842 | | 2/2004 |
| WO | WO 2004/033453 | | 4/2004 |
| WO | WO 2004/087641 | | 10/2004 |
| WO | WO 2004/094425 | | 11/2004 |
| WO | WO 2005/086808 | | 9/2005 |
| WO | 2006088246 | * | 8/2006 |
| WO | WO 2006/088246 | | 8/2006 |
| WO | 2008011130 | * | 1/2008 |
| WO | 2008029152 | * | 3/2008 |

OTHER PUBLICATIONS

Klupsch et al., Chemical & Pharmaceutical Bulletin (2006), 54(9), 1318-1321.*
Fisher et al., Journal of Medicinal Chemistry (1972), 15(9), 982-5.*
Enguehard-Gueiffier et al., Tetrahedron (2006), 62(25), 6042-6049.*
Sundberg et al., Journal of Heterocyclic Chemistry (1988), 25(1), 129-37.*
Tomoda et al., Bulletin of the Chemical Society of Japan (1999), 72(6), 1327-1334.*
Buu-Hoi et al., Journal of the Chemical Society (1958) 2815-21.*
Zhuang, et. al., Structure-Activity Relationship of Imidazo[1,2-a]pyridines as Ligands for Detecting Beta-Amyloid Plaques in the Brain, J. Med. Chem., 2003 (46) pp. 237-243.
Bose, D.S., et. al., A Practical Method for the Preparation of Nitriles from Primary Amides Under Non-Acidic Conditions, Synthesis, 1999 (1) pp. 64-65.

(Continued)

*Primary Examiner* — Niloofar Rahmani
(74) *Attorney, Agent, or Firm* — Ronald G. Ort; Scully, Scott, Murphy & Presser, P.C.

(57) ABSTRACT

The present invention relates to derivatives of imidazo[1,2-a] pyridines of formula I,

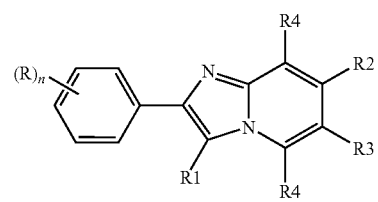

in which R, R1 to R4 and n have the meanings indicated in the claims, which modulate the transcription of endothelial nitric oxide (NO) synthase and are valuable pharmacologically active compounds. Specifically, the compounds of formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of formula I, to pharmaceutical compositions comprising them, and to the use of compounds of formula I for the stimulation of the expression of endothelial NO synthase or for the treatment of various diseases including cardiovascular disorders such as atherosclerosis, thrombosis, coronary artery disease, hypertension and cardiac insufficiency, for example.

7 Claims, No Drawings

OTHER PUBLICATIONS

Cai, et. al., Rapid Palladium-catalyzed cross-coupling in the synthesis of aryl thioethers under microwave conditions, Tetrahedron Letters, 2006 (47) pp. 4449-4452.

Endres, et. al., Stroke Protection by 3-Hydroxy-3-Methylglutaryl (HMG)-CoA Reductase Inhibitors Medicated by Endothelial Nitric Oxide Synthase, PNAS USA 1998 (95) pp. 8880-8885.

Enguehard-Gueiffier, et. al., A general and efficient method for the copper-catalyzed cross-coupling of amides and thiophenols with 6-halogenoimidazo[1,2-a]pyridines, Tetrahedron, 2006 (62), pp. 6042-6049.

Fisher et al, Imidazo[1,2-a]pyridine Anthelmintic and Antifungal Agents, J.Med.Chem., 1972 (15) 9, pp. 982-985.

Gerencser, et. al., Procedure for the Parallel Preparation of 3-Imidazo[1,2-a]pyridin-3-yl-propionic Acid Derivatives Involving Meldrum's Acid. J. Comb. Chem., 2005 (7) pp. 530-538.

Gueiffier, et. al., Synthesis of 1H-Imidazo[1,2-a]pyrazolo[3,4-c]pyridines, Chem. Pharm. Bull., 1990 (38) 9, pp. 2353-2356.

Kazzouli, et. al., Solid-phase synthesis of imidazo[1,2-a]pyridines and imidazo[1,2-a]pyrimidines, Tetra. Letters, 2003 (44) 33, pp. 6265-6267.

Li et al, Activation of Protein Kinase Cα and or ε Enhances Transcription of the Human Endothelial Nitric Oxide Synthase Gene, Mol. Pharmacol., 1998 (53) pp. 630-637.

Li, et. al., Discovery of Potent 3,5-Diphenyl-1,2,4-oxadiazole Sphingosine-1-phosphate-1 (S1P1) Receptor Agonists with Exceptional Selectivity against S1P2 and S1P3, J. Med. Chem., 2005 (48) 20, pp. 6169-6173.

Moroi, et. al., Interaction of Genetic Deficiency of Endothelial Nitric Oxide, Gender, and Pregnancy in Vascular Response to Injury in Mice, J. Clin. Invest., 1998 (101) 6 pp. 1225-1232.

Nakayama, et. al., T-786→C Mutation in the 5'-Flanking Region of the Endothelial Nitric Oxide Synthase Gene is Associated With Coronary Spasm, Circulation 1999 (99) pp. 2864-2870.

Sanfilippo, et. al., Synthesis of (Aryloxy)alkylamines. 2. Novel Imidazo-fused Heterocycles with Calcium Channel Blocking and Local Anesthetic Activity, J. Med. Chem., 1988 (31) 11, pp. 2221-2227.

Sessa, et. al., Chronic Exercise in Dogs Increases Coronary Vascular Nitric Oxide Production and Endothelial Cell Nitric Oxide Synthase Gene Expression, Circ. Res., 1994 (74) 2, pp. 349-353.

Sundberg, et. al., Bis-Cationic Heteroaromatics as Macrofilaricides: Synthesis of Bis-Amidine and Bis-Guanyihydrazone Derivatives of Substituted Imidazo[1,2-a]pyridines, J.Med.Chem., 1988 (41) pp. 4317-4328.

Sundberg, et. al., Preparation of 2-Aryl and 2-Aryloxymethyl lmidazo[1,2-a]pyridines and Related Compounds, J. Heterocyclic Chem., 1988 (25) pp. 129-137.

Trapani, et. al., Synthesis and Binding Affinity of 2-Phenylimidazo[1,2-a]pyridine Derivatives for both Central and Peripheral Benzodiazepine Receptors. A New Series of High-Affinity and Selective Ligands for the Peripheral Type, J. Med. Chem., 1997 (40) 9, pp. 3109-3118.

Varenne, et. al., Percutaneous Gene Therapy Using Recombinant Adenoviruses Encoding Human Herpes Simplex Virus Thymidine Kinase, Human PAI-1, and Human NOS3 in Balloon-Injured Porcine Coronary Arteries, Hum. Gene Ther. 2000 (11) pp. 1329-1339.

Bjorklund, M. D., et. al., 3,3-Dinitrobutyl-1,2,4-oxadiazoles (1), J. Heterocyclic Chem., 1980 (14) 4, pp. 819-821.

Buu-Hoi, N. P., et. al., No. 208.—Sur Quelques Derives Fonctionnels du Pyrimidazole et de L'aza-8 Pyrimidazole, Bull.Soc.Chim.France, 1961 pp. 1344-1346.

Ferrari, G., et. al., Studi Nella Serie Della Piridina. Farmaco, Ed.Sci., 1963 (18) 1, pp. 42-46.

Kazzouli, S., et. al., Solution and Solid Phase Functionalization of Imidazo [1,2-a]Pyridines, Letters in Organic Chemistry, vol. 2, pp. 184-187, (2005).

Lu, et. al., Synthesis and Biodistribution of [131I]IMPY, Nuclear Science and Techriques. vol. 16, No. 5, (2005) pp. 289-292.

Wagner, G., et. al., Synthese Von 3-[Amidinophenyl]-Alaninen Und 3-[Amidinophenyl]-Milchsauren1, Pharmazie, vol. 29, No. 1, (1974), pp. 12-15.

* cited by examiner

IMIDAZO[1,2-A]PYRIDINES AND THEIR USE AS PHARMACEUTICALS

FIELD OF THE INVENTION

The present invention relates to derivatives of imidazo[1,2-a]pyridines of formula I,

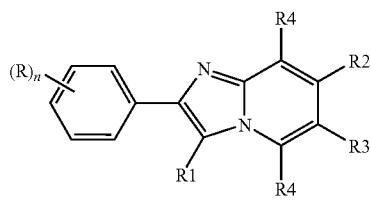

in which R, R1 to R4 and n have the meanings indicated below, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

BACKGROUND OF THE INVENTION

Endothelial NO synthase (eNOS, NOS-III) belongs to a group of three isoenzymes which produce nitric oxide (nitrogen monoxide, NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349) were able to obtain a marked increase in eNOS by means of exercise training and the increase in shear stress associated therewith.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering, also in part to an increase in eNOS expression in vivo (Endres et al., Proc. Natl. Acad. Sci. USA 95 (1998) 8880). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. For the statins, as has already been mentioned, it has been possible to show such an increase in eNOS in vivo as a side effect. In view of the known range of side effects of this class of substances, however, it is unclear how far use of this effect can be made in a toxicologically unproblematic dose. Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension without, however, indicating a specific way of achieving this. Certain amide derivatives which upregulate the expression of endothelial NO synthase, in particular N-cycloalkyl amides in which the cycloalkyl ring is fused to a benzene ring or a heteroaromatic ring, have been described in WO 02/064146, WO 02/064545, WO 02/064546, WO 02/064565, WO 2004/014369, WO 2004/014372 and WO 2004/014842. Certain triaza- and tetraaza-anthracenedione derivatives which upregulate the expression of endothelial NO synthase have been described in WO 2004/094425. There still exists a need for further compounds which upregulate the expression of endothelial NO synthase and have a favorable property profile and are useful as pharmaceuticals for the treatment of various diseases such as atherosclerosis, coronary artery disease or cardiac insufficiency, for example.

Surprisingly it has now been found that the compounds of the formula I are modulators of the transcription of endothelial NO synthase and in particular stimulate, or upregulate, the expression of eNOS, and are useful for the treatment of various diseases such as the mentioned cardiovascular disorders.

Certain compounds which are encompassed by the formula I, are described in a number of documents including EP 668278; WO 2006/088246; WO 02/085903; WO 2003/000689; WO 02/066477; FR 2606409; EP 267111; WO 2005/086808; WO 2004/087641; WO 2003/04188; WO 2003/000689; U.S. Pat. No. 4,767,755; Journal of Medicinal Chemistry (1972), 15(9), 982-5; Farmaco, Edizione Scientifica (1963), 18(1), 42-6; Bull. Soc. Chim. France (1961), 1344-6; Journal of Medicinal Chemistry (1998), 41(22), 4317-4328; Tetrahedron (2006), 62(25), 6042-6049; Chemical & Pharmaceutical Bulletin (1990), 38(9), 2352-6; Journal of Heterocyclic Chemistry (1988), 25(1), 129-37; Tetrahedron Letters (2006), 47(26), 4449-4452; Nuclear Science and Techniques (2005), 16(5), 289-292; Journal of Combinatorial Chemistry (2005), 7(4), 530-538; Letters in Organic Chemistry (2005), 2(2), 184-187; Tetrahedron Letters (2003), 44(33), 6265-6267; Journal of Medicinal Chemistry (2003), 46(2), 237-243. A stimulating effect of these known compounds of the formula I on the transcription or the expression of eNOS and their use in the treatment of diseases which is based on such effect, has not yet been described.

DETAILED DESCRIPTION OF THE INVENTION

A subject of the present invention is the use of a compound of the formula I,

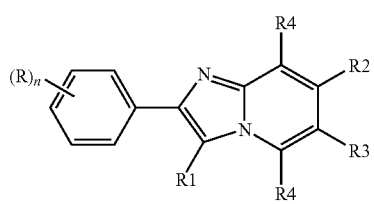

in which
R is chosen from halogen, $(C_1-C_6)$-alkyl which can be substituted by one or more fluorine atoms, $(C_1-C_3)$-alkoxy-$(C_1-C_3)$-alkyl, hydroxy, $(C_1-C_6)$-alkoxy which can be substituted by one or more fluorine atoms, $(C_1-C_6)$-alkylmercapto, NR7R8, mono-$(C_1-C_6)$-alkylaminocarbonyl, di-$(C_2-C_6)$-alkylaminocarbonyl, $(C_1-C_6)$-alkoxycarbonyl, cyano, $(C_1-C_6)$-alkylsulfinyl, $(C_1-C_6)$-alkylsulfonyl, aminosulfonyl, nitro, pentafluorosulfanyl, $(C_3-C_7)$-cycloalkyl and $(C_6-C_{14})$-aryl, wherein the aryl residue can be substituted by one or more identical or different substituents chosen from halogen, $(C_1-C_6)$-alkyl, $(C_1-C_6)$-alkoxy and trifluoromethyl;
or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, and —S(O)$_2$— cannot be present in adjacent ring positions;
R1 is chosen from hydrogen and $(C_1-C_6)$-alkyl;
or R and R1 form together a $(C_1-C_2)$-alkylene or $(C_1-C_2)$-alkenylene chain if R is attached in ortho-position of the phenyl ring;
R2 is chosen from hydrogen, hydroxy and $(C_1-C_6)$-alkyl;
R3 is chosen from Br, cyano, nitro, —C(=O)—NR9R10, amino, —N(R11)-C(=O)—R12, COOH, $(C_1-C_6)$-alkoxycarbonyl and —C(=NR5)-NHR6;
R4 is each time independently chosen from hydrogen and $(C_1-C_6)$-alkyl;
R5 is chosen from hydrogen, $(C_1-C_6)$-alkyl, $(C_1-C_6)$-alkylcarbonyl, $(C_1-C_6)$-alkoxycarbonyl, $(C_1-C_6)$-alkoxycarbonyloxy, $(C_1-C_{18})$-alkylcarbonyloxy-$(C_1-C_6)$-alkoxycarbonyl, $(C_6-C_{14})$-arylcarbonyl, $(C_6-C_{14})$-aryloxycarbonyl, hydroxy, $(C_1-C_6)$-alkylcarbonyloxy, $(C_6-C_{14})$-aryl-$(C_1-C_6)$-alkoxycarbonyl, $(C_1-C_6)$-alkylaminocarbonyloxy, di-(($C_1-C_6$)-alkyl)aminocarbonyloxy, $(C_1-C_6)$-alkylaminocarbonyl and di-(($C_1-C_6$)-alkyl)aminocarbonyl, wherein all aryl groups can be substituted by one or more identical or different substituents chosen from halogen, $(C_1-C_6)$-alkyl, $(C_1-C_6)$-alkoxy and trifluoromethyl;
R6 is chosen from hydrogen, cyano, hydroxy, $(C_1-C_6)$-alkoxy and $(C_6-C_{14})$-aryl-$(C_1-C_6)$ alkoxy;
or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R7 and R8 are independently chosen from hydrogen and $(C_1-C_6)$-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and $(C_1-C_6)$-alkyl;
or R9 and R10 form, together with the nitrogen atom which carries them, a 4-membered to 7-membered, saturated, partially unsaturated or aromatic heterocyclic ring;
R11 is chosen from hydrogen and $(C_1-C_6)$-alkyl;
R12 is chosen from hydrogen and $(C_1-C_6)$-alkyl;
or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R13, R14 and R15 are independently chosen from halogen, $(C_1-C_6)$-alkyl, $(C_1-C_6)$-alkoxy and trifluoromethyl;
n is chosen from 0, 1, 2, 3, 4 and 5;
in any of its stereoisomeric forms or a mixture of stereoisomeric forms in any ratio, or a physiologically acceptable salt thereof, for the manufacture of a medicament for the stimulation of the expression of endothelial NO synthase or for the treatment of a disease in which such a stimulation, or an increase in NO level, is desired, for example a cardiovascular disorder such as atherosclerosis, coronary artery disease or cardiac insufficiency or any other disease mentioned above or below herein.

Another subject of the present invention is the use of a compound of the formula I,

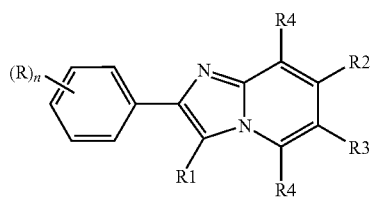

in which
R is chosen from halogen, $(C_1\text{-}C_6)$-alkyl which can be substituted by one or more fluorine atoms, $(C_1\text{-}C_3)$-alkoxy-$(C_1\text{-}C_3)$-alkyl, hydroxy, $(C_1\text{-}C_6)$-alkoxy which can be substituted by one or more fluorine atoms, $(C_1\text{-}C_6)$-alkylmercapto, NR7R8, mono-$(C_1\text{-}C_6)$-alkylaminocarbonyl, di-$(C_2\text{-}C_6)$-alkylaminocarbonyl, $(C_1\text{-}C_6)$-alkoxycarbonyl, cyano, $(C_1\text{-}C_6)$-alkylsulfinyl, $(C_1\text{-}C_6)$-alkylsulfonyl, aminosulfonyl, nitro, pentafluorosulfanyl, $(C_3\text{-}C_7)$-cycloalkyl and $(C_6\text{-}C_{14})$-aryl, wherein the aryl residue can be substituted by one or more identical or different substituents chosen from halogen, $(C_1\text{-}C_6)$-alkyl, $(C_1\text{-}C_6)$-alkoxy and trifluoromethyl;
or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R1 is chosen from hydrogen and $(C_1\text{-}C_6)$-alkyl;
or R and R1 form together a $(C_1\text{-}C_2)$-alkylene or $(C_1\text{-}C_2)$-alkenylene chain if R is attached in ortho-position of the phenyl ring;
R2 is chosen from hydrogen, hydroxy and $(C_1\text{-}C_6)$-alkyl;
R3 is chosen from Br, cyano, nitro, —C(=O)—NR9R10, amino, —N(R11)-C(=O)—R12, COOH, $(C_1\text{-}C_6)$-alkoxycarbonyl and —C(=NR5)-NHR6;
R4 is each time independently chosen from hydrogen and $(C_1\text{-}C_6)$-alkyl;
R5 is chosen from hydrogen, $(C_1\text{-}C_6)$-alkyl, $(C_1\text{-}C_6)$-alkylcarbonyl, $(C_1\text{-}C_6)$-alkoxycarbonyl, $(C_1\text{-}C_6)$-alkoxycarbonyloxy, $(C_1\text{-}C_{18})$-alkylcarbonyloxy-$(C_1\text{-}C_6)$-alkoxycarbonyl, $(C_6\text{-}C_{14})$-arylcarbonyl, $(C_6\text{-}C_{14})$-aryloxycarbonyl, hydroxy, $(C_1\text{-}C_6)$-alkylcarbonyloxy, $(C_6\text{-}C_{14})$-aryl-$(C_1\text{-}C_6)$-alkoxycarbonyl, $(C_1\text{-}C_6)$-alkylaminocarbonyloxy, di-$((C_1\text{-}C_6)$-alkyl)aminocarbonyloxy, $(C_1\text{-}C_6)$-alkylaminocarbonyl and di-$((C_1\text{-}C_6)$-alkyl)aminocarbonyl, wherein all aryl groups can be substituted by one or more identical or different substituents chosen from halogen, $(C_1\text{-}C_6)$-alkyl, $(C_1\text{-}C_6)$-alkoxy and trifluoromethyl;
R6 is chosen from hydrogen, cyano, hydroxy, $(C_1\text{-}C_6)$-alkoxy and $(C_6\text{-}C_{14})$-aryl-$(C_1\text{-}C_6)$ alkoxy;
or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R7 and R8 are independently chosen from hydrogen and $(C_1\text{-}C_6)$-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and $(C_1\text{-}C_6)$-alkyl;
or R9 and R10 form, together with the nitrogen atom which carries them, a 4-membered to 7-membered, saturated, partially unsaturated or aromatic heterocyclic ring;
R11 is chosen from hydrogen and $(C_1\text{-}C_6)$-alkyl;
R12 is chosen from hydrogen and $(C_1\text{-}C_6)$-alkyl;
or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R13, R14 and R15 are independently chosen from halogen, $(C_1\text{-}C_6)$-alkyl, $(C_1\text{-}C_6)$-alkoxy and trifluoromethyl;
n is chosen from 0, 1, 2, 3, 4 and 5;
in any of its stereoisomeric forms or a mixture of stereoisomeric forms in any ratio, or a physiologically acceptable salt thereof, for the manufacture of a medicament for the stimulation of the expression of endothelial NO synthase or for the treatment of a disease in which such a stimulation, or an increase in NO level, is desired, for example a cardiovascular disorder such as atherosclerosis, coronary artery disease or cardiac insufficiency or any other disease mentioned above or below herein,
provided that 2-(4-cyano-phenyl)-imidazo[1,2-a]pyridine-6-carboxylic acid is excluded,
and provided that compounds are excluded in which R1 is hydrogen or methyl, R2 and R4 are hydrogen, n is 1, R3 is COOH or $(C_1\text{-}C_6)$-alkoxycarbonyl and R is Cl.

A preferred embodiment of the present invention relates to the use of a compound of the formula I, in which
R is chosen from halogen, $(C_1\text{-}C_6)$-alkyl which can be substituted by one or more fluorine atoms, $(C_1\text{-}C_6)$-alkoxy which can be substituted by one or more fluorine atoms, NR7R8, cyano, $(C_1\text{-}C_6)$-alkylsulfonyl, aminosulfonyl, nitro, $(C_3\text{-}C_7)$-cycloalkyl and $(C_6\text{-}C_{14})$-aryl, wherein the aryl residue can be substituted by one or more identical or different substituents chosen from halogen, $(C_1\text{-}C_6)$-alkyl, $(C_1\text{-}C_6)$-alkoxy and trifluoromethyl;
or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R1 is chosen from hydrogen and $(C_1\text{-}C_6)$-alkyl;

or R and R1 form together a $(C_1$-$C_2)$-alkylene chain if R is attached in ortho-position of the phenyl ring;
R2 is hydrogen;
R3 is chosen from Br, cyano, nitro, —C(=O)—NR9R10, amino, —N(R11)-C(=O)—R12, COOH, $(C_1$-$C_6)$-alkoxycarbonyl and —C(=NR5)-NHR6;
R4 is each time hydrogen;
R5 is chosen from hydrogen, $(C_1$-$C_6)$-alkoxycarbonyloxy and hydroxy;
R6 is hydrogen;
or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R7 and R8 are independently chosen from hydrogen and $(C_1$-$C_6)$-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and $(C_1$-$C_6)$-alkyl;
or R9 and R10 form, together with the nitrogen atom which carries them, a 4-membered to 7-membered, saturated, partially unsaturated or aromatic heterocyclic ring;
R11 is hydrogen;
R12 is chosen from hydrogen and $(C_1$-$C_6)$-alkyl;
or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R13, R14 and R15 are independently chosen from halogen, $(C_1$-$C_6)$-alkyl, $(C_1$-$C_6)$-alkoxy and trifluoromethyl;
n is chosen from 0, 1, 2, 3, 4 and 5;
in any of its stereoisomeric forms or a mixture of stereoisomeric forms in any ratio, or a physiologically acceptable salt thereof, for the manufacture of a medicament for the stimulation of the expression of endothelial NO synthase or for the treatment of a disease in which such a stimulation, or an increase in NO level, is desired, for example a cardiovascular disorder such as atherosclerosis, coronary artery disease or cardiac insufficiency or any other disease mentioned above or below herein, provided that 2-(4-cyano-phenyl)-imidazo[1,2-a]pyridine-6-carboxylic acid is excluded, and provided that compounds are excluded in which R1 is hydrogen or methyl, R2 and R4 are hydrogen, n is 1, R3 is COOH or $(C_1$-$C_6)$-alkoxycarbonyl and R is Cl.

A more preferred embodiment of the present invention relates to the use of a compound of the formula I, in which R is chosen from halogen, $(C_1$-$C_6)$-alkyl which can be substituted by one or more fluorine atoms, $(C_1$-$C_6)$-alkoxy which can be substituted by one or more fluorine atoms, NR7R8, cyano, $(C_1$-$C_6)$-alkylsulfonyl, aminosulfonyl, nitro, $(C_3$-$C_7)$-cycloalkyl and $(C_6$-$C_{14})$-aryl;

or two adjacent R groups form, together with the carbon atoms which carry them, a 4-membered to 7-membered, partially unsaturated or aromatic heterocyclic ring and which can contain one or two ring members chosen from —N(R4)-, —C(=O)— or —O— which can be identical or different;
R1 is chosen from hydrogen and $(C_1$-$C_6)$-alkyl;
or R and R1 form together a $(C_1$-$C_2)$-alkylene chain if R is attached in ortho-position of the phenyl ring;
R2 is hydrogen;
R3 is chosen from Br, cyano, nitro, —C(=O)—NR9R10, amino, —N(R11)-C(=O)—R12, COOH, $(C_1$-$C_6)$-alkoxycarbonyl and —C(=NR5)-NHR6;
R4 is each time hydrogen;
R5 is chosen from hydrogen, $(C_1$-$C_6)$-alkoxycarbonyloxy and hydroxy;
R6 is hydrogen;
or R5 and R6 form, together with the —N=C—NH— group which carries them, a 4-membered to 7-membered, partially unsaturated or aromatic heterocyclic ring and which, in addition to the nitrogen atoms being part of the —N=C—NH— group, can contain one or two further ring members chosen from —C(=O)— and —O—;
R7 and R8 are independently chosen from hydrogen and $(C_1$-$C_6)$-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and $(C_1$-$C_6)$-alkyl;
or R9 and R10 form, together with the nitrogen atom which carries them, a 4-membered to 7-membered, saturated, partially unsaturated or aromatic heterocyclic ring;
R11 is hydrogen;
R12 is chosen from hydrogen and $(C_1$-$C_6)$-alkyl;
or R11 and R12 form, together with the carbonylamino group which carries them, a 4-membered to 7-membered, saturated, partially unsaturated or aromatic heterocyclic ring and which, in addition to the carbonylamino group connecting R11 and R12, can contain one or two further ring members chosen from —N(R4)- and —C(=O)—;
n is chosen from 0, 1, 2, 3, 4 and 5;
in any of its stereoisomeric forms or a mixture of stereoisomeric forms in any ratio, or a physiologically acceptable salt thereof, for the manufacture of a medicament for the stimulation of the expression of endothelial NO synthase or for the treatment of a disease in which such a stimulation, or an increase in NO level, is desired, for example a cardiovascular disorder such as atherosclerosis, coronary artery disease or cardiac insufficiency or any other disease mentioned above or below herein, provided that 2-(4-cyano-phenyl)-imidazo[1,2-a]pyridine-6-carboxylic acid is excluded, and provided that compounds are excluded in which R1 is hydrogen or methyl, R2 and R4 are hydrogen, n is 1, R3 is COOH or $(C_1$-$C_6)$-alkoxycarbonyl and R is Cl.

Another preferred embodiment of the present invention relates to the use of a compound of the formula I, wherein the compound of the formula I is chosen from:
2-(4-fluoro-phenyl)-imidazo[1,2-a]pyridine-6-carboxylic acid methyl ester,
2-(4-bromo-phenyl)-3-methyl-imidazo[1,2-a]pyridine-6-carboxylic acid methyl ester,
3-methyl-2-phenyl-imidazo[1,2-a]pyridine-6-carboxylic acid methyl ester,
2-(2-oxo-1,2,3,4-tetrahydro-quinolin-6-yl)-imidazo[1,2-a]pyridine-6-carboxylic acid methyl ester,
2-(2-fluoro-phenyl)-imidazo[1,2-a]pyridine-6-carboxylic acid methyl ester, 2-pentafluoro-phenyl-imidazo[1,2-a]pyridine-6-carboxylic acid methyl ester,
2-p-tolyl-imidazo[1,2-a]pyridine-6-carboxylic acid methyl ester,
2-(3-chloro-phenyl)-imidazo[1,2-a]pyridine-6-carbonitrile
2-(3-nitro-phenyl)-imidazo[1,2-a]pyridine-6-carboxylic acid methyl ester,
2-(4-methoxy-phenyl)-imidazo[1,2-a]pyridine-6-carboxylic acid methyl ester,
2-naphthalen-2-yl-imidazo[1,2-a]pyridine-6-carboxylic acid methyl ester,
2-(4-bromo-phenyl)-imidazo[1,2-a]pyridine-6-carboxylic acid methyl ester,
2-phenyl-imidazo[1,2-a]pyridine-6-carboxylic acid methyl ester,
2-(3-fluoro-phenyl)-imidazo[1,2-a]pyridine-6-carboxylic acid methyl ester,
2-(4-trifluoromethyl-phenyl)-imidazo[1,2-a]pyridine-6-carboxylic acid methyl ester,
2-(4-trifluoromethoxy-phenyl)-imidazo[1,2-a]pyridine-6-carboxylic acid methyl ester,
2-(4-diethylamino-phenyl)-imidazo[1,2-a]pyridine-6-carboxylic acid methyl ester,
2-(4-cyano-phenyl)-imidazo[1,2-a]pyridine-6-carboxylic acid methyl ester,
2-(2-chloro-phenyl)-imidazo[1,2-a]pyridine-6-carboxylic acid methyl ester,
2-(4-bromo-3-sulfamoyl-phenyl)-imidazo[1,2-a]pyridine-6-carboxylic acid methyl ester,
2-(4-fluoro-3-sulfamoyl-phenyl)-imidazo[1,2-a]pyridine-6-carboxylic acid methyl ester,
2-(3-cyano-phenyl)-imidazo[1,2-a]pyridine-6-carboxylic acid methyl ester,
2-(3-bromo-phenyl)-imidazo[1,2-a]pyridine-6-carboxylic acid methyl ester,
2-(2,4-dimethyl-phenyl)-imidazo[1,2-a]pyridine-6-carboxylic acid methyl ester,
2-(3,4-dichloro-phenyl)-imidazo[1,2-a]pyridine-6-carboxylic acid methyl ester,
2-(4-chloro-3-methyl-phenyl)-imidazo[1,2-a]pyridine-6-carboxylic acid methyl ester,
2-(2,4-dichloro-phenyl)-imidazo[1,2-a]pyridine-6-carboxylic acid methyl ester,
2-(4-cyclohexyl-phenyl)-imidazo[1,2-a]pyridine-6-carboxylic acid methyl ester,
2-(4-methanesulfonyl-phenyl)-imidazo[1,2-a]pyridine-6-carboxylic acid methyl ester,
2-(3-chloro-phenyl)-imidazo[1,2-a]pyridine-6-carboxylic acid methyl ester,
2-(3,5-difluoro-phenyl)-imidazo[1,2-a]pyridine-6-carboxylic acid methyl ester,
2-(3-trifluoromethyl-phenyl)-imidazo[1,2-a]pyridine-6-carboxylic acid methyl ester,
2-(2,3-dihydro-benzo[1,4]dioxin-6-yl)-imidazo[1,2-a]pyridine-6-carboxylic acid methyl ester,
2-(2,6-dichloro-4-trifluoromethyl-phenyl)-imidazo[1,2-a]pyridine-6-carboxylic acid methyl ester,
2-(2-nitro-phenyl)-imidazo[1,2-a]pyridine-6-carboxylic acid methyl ester,
2-biphenyl-4-yl-imidazo[1,2-a]pyridine-6-carboxylic acid methyl ester,
2-(4-nitro-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(2-trifluoromethyl-phenyl)-imidazo[1,2-a]pyridine-6-carboxylic acid methyl ester,
11H-indeno[1',2':4,5]imidazo[1,2-a]pyridine-8-carboxylic acid methyl ester,
2-(4-pyrrolidin-1-yl-phenyl)-imidazo[1,2-a]pyridine-6-carboxylic acid methyl ester,
2-(4-amino-phenyl)-imidazo[1,2-a]pyridine-6-carboxylic acid methyl ester,
2-(4-fluoro-phenyl)-imidazo[1,2-a]pyridine-6-carboxylic acid,
2-p-tolyl-imidazo[1,2-a]pyridine-6-carboxylic acid,
2-(4-diethylamino-phenyl)-imidazo[1,2-a]pyridine-6-carboxylic acid,
2-(4-fluoro-phenyl)-imidazo[1,2-a]pyridine-6-carboxylic acid tert-butylamide,
2-(4-fluoro-phenyl)-imidazo[1,2-a]pyridine-6-carboxylic acid amide,
2-(4-fluoro-phenyl)-imidazo[1,2-a]pyridine-6-carboxylic acid dimethylamide,
azetidin-1-yl-[2-(4-fluoro-phenyl)-imidazo[1,2-a]pyridin-6-yl]-methanone,
2-(4-fluoro-phenyl)-imidazo[1,2-a]pyridine-6-carbonitrile,
2-(4-diethylamino-phenyl)-imidazo[1,2-a]pyridine-6-carbonitrile,
2-p-tolyl-imidazo[1,2-a]pyridine-6-carbonitrile,
2-(3-chloro-phenyl)-imidazo[1,2-a]pyridine-6-carbonitrile,
2-(4-fluoro-phenyl)-N-hydroxy-imidazo[1,2-a]pyridine-6-carboxamidine,
N-hydroxy-2-p-tolyl-imidazo[1,2-a]pyridine-6-carboxamidine,
2-(4-diethylamino-phenyl)-N-hydroxy-imidazo[1,2-a]pyridine-6-carboxamidine,
2-(3-chloro-phenyl)-N-hydroxy-imidazo[1,2-a]pyridine-6-carboxamidine,
2-(4-fluoro-phenyl)-N-ethoxycarbonyloxy-imidazo[1,2-a]pyridine-6-carboxamidine,
6-bromo-2-(4-fluoro-phenyl)-imidazo[1,2-a]pyridine,
6-bromo-2-p-tolyl-imidazo[1,2-a]pyridine,
6-bromo-2-(3-chloro-phenyl)-imidazo[1,2-a]pyridine,
[4-(6-bromo-imidazo[1,2-a]pyridin-2-yl)phenyl]-diethyl-amine,
2-(4-fluoro-phenyl)-6-nitro-imidazo[1,2-a]pyridine,
2-(4-fluoro-phenyl)-imidazo[1,2-a]pyridin-6-ylamine,
N-[2-(4-fluoro-phenyl)-imidazo[1,2-a]pyridin-6-yl]-formamide,
N-[2-(4-fluoro-phenyl)-imidazo[1,2-a]pyridin-6-yl]-acetamide,
3-[2-(4-fluoro-phenyl)-imidazo[1,2-a]pyridin-6-yl]-imidazolidine-2,4-dione,
3-[2-(4-fluoro-phenyl)-imidazo[1,2-a]pyridin-6-yl]-4H-1,2,4-oxadiazol-5-one, and
2-(4-fluoro-phenyl)-imidazo[1,2-a]pyridine-6-carboxamidine, in any of its stereoisomeric forms or a mixture of stereoisomeric forms in any ratio, or a physiologically acceptable salt thereof, for the manufacture of a medicament for the stimulation of the expression of endothelial NO synthase or for the treatment of a disease in which such a stimulation, or an increase in NO level, is desired, for example a cardiovascular disorder such as atherosclerosis, coronary artery disease or cardiac insufficiency or any other disease mentioned above or below herein.

Another embodiment of the present invention relates to the use of a compound of the formula I in any of its stereoisomeric forms or a mixture of stereoisomeric forms in any ratio, or a physiologically acceptable salt thereof, for the manufacture of a medicament for the stimulation of the expression of endothelial NO synthase or for the treatment of a disease in which such a stimulation, or an increase in NO level, is desired, for example a cardiovascular disorder such as atherosclerosis, coronary artery disease or cardiac insufficiency or any other disease mentioned above or below herein, wherein the compound of the formula I is a compound of the formula Ia or Ib as defined below.

Another subject of the present invention relates to a compound of the formula Ia,

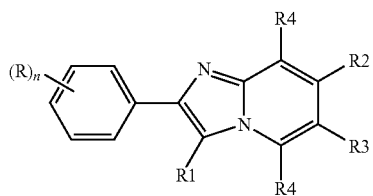

in any of its stereoisomeric forms or a mixture of stereoisomeric forms in any ratio, or a physiologically acceptable salt thereof, for use as a pharmaceutical, in which R is chosen from halogen, $(C_1-C_6)$-alkyl which can be substituted by one or more fluorine atoms, $(C_1-C_3)$-alkoxy-$(C_1-C_3)$-alkyl, hydroxy, $(C_1-C_6)$-alkoxy which can be substituted by one or more fluorine atoms, $(C_1-C_6)$-alkylmercapto, NR7R8, mono-$(C_1-C_6)$-alkylaminocarbonyl, di-$(C_2-C_6)$-alkylaminocarbonyl, $(C_1-C_6)$-alkoxycarbonyl, cyano, $(C_1-C_6)$-alkylsulfinyl, $(C_1-C_6)$-alkylsulfonyl, aminosulfonyl, nitro, pentafluorosulfanyl, $(C_3-C_7)$-cycloalkyl and $(C_6-C_{14})$-aryl, wherein the aryl residue can be substituted by one or more identical or different substituents chosen from halogen, $(C_1-C_6)$-alkyl, $(C_1-C_6)$-alkoxy and trifluoromethyl;

or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;

R1 is chosen from hydrogen and $(C_1-C_6)$-alkyl;

or R and R1 form together a $(C_1-C_2)$-alkylene or $(C_1-C_2)$-alkenylene chain if R is attached in ortho-position of the phenyl ring;

R2 is chosen from hydrogen, hydroxy and $(C_1-C_6)$-alkyl;

R3 is chosen from Br, cyano, nitro, —C(=O)—NR9R10, amino, —N(R11)-C(=O)—R12, COOH, $(C_1-C_6)$-alkoxycarbonyl and —C(=NR5)-NHR6;

R4 is each time independently chosen from hydrogen and $(C_1-C_6)$-alkyl;

R5 is chosen from hydrogen, $(C_1-C_6)$-alkyl, $(C_1-C_6)$-alkylcarbonyl, $(C_1-C_6)$-alkoxycarbonyl, $(C_1-C_6)$-alkoxycarbonyloxy, $(C_1-C_{18})$-alkylcarbonyloxy-$(C_1-C_6)$-alkoxycarbonyl, $(C_6-C_{14})$-arylcarbonyl, $(C_6-C_{14})$-aryloxycarbonyl, hydroxy, $(C_1-C_6)$-alkylcarbonyloxy, $(C_6-C_{14})$-aryl-$(C_1-C_6)$-alkoxycarbonyl, $(C_1-C_6)$-alkylaminocarbonyloxy, di-(($C_1-C_6)$-alkyl)aminocarbonyloxy, $(C_1-C_6)$-alkylaminocarbonyl and di-(($C_1-C_6)$-alkyl)aminocarbonyl, wherein all aryl groups can be substituted by one or more identical or different substituents chosen from halogen, $(C_1-C_6)$-alkyl, $(C_1-C_6)$-alkoxy and trifluoromethyl;

R6 is chosen from hydrogen, cyano, hydroxy, $(C_1-C_6)$-alkoxy and $(C_6-C_{14})$-aryl-$(C_1-C_6)$ alkoxy;

or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;

R7 and R8 are independently chosen from hydrogen and $(C_1-C_6)$-alkyl;

or R7 and R8 form, together with the nitrogen atom which carries them, a 4-membered to 7-membered, saturated, partially unsaturated or aromatic heterocyclic ring;

R9 and R10 are independently chosen from hydrogen and $(C_1-C_6)$-alkyl;

or R9 and R10 form, together with the nitrogen atom which carries them, a 4-membered to 7-membered, saturated, partially unsaturated or aromatic heterocyclic ring;

R11 is chosen from hydrogen and $(C_1-C_6)$-alkyl;

R12 is chosen from hydrogen and $(C_1-C_6)$-alkyl;

or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;

R13, R14 and R15 are independently chosen from halogen, $(C_1-C_6)$-alkyl, $(C_1-C_6)$-alkoxy and trifluoromethyl;

n is chosen from 0, 1, 2, 3, 4 and 5;

provided that compounds are excluded in which R1, R2 and R4 are hydrogen, n is 1, R is cyano and R3 is cyano or COOH, provided that compounds are excluded in which R1 is hydrogen or methyl, R2 and R4 are hydrogen, n is 1, R3 is COOH or $(C_1-C_6)$-alkoxycarbonyl and R is Cl, provided that compounds are excluded in which R1, R2 and R4 are hydrogen and n is 0, and provided that compounds are excluded in which R1, R2 and R4 are hydrogen, R3 is Br, n is 1 and R is Br, NO$_2$, dimethylamino, amino, methyl, amide (CONH$_2$) or F.

A preferred embodiment of the present invention relates to a compound of the formula Ia, in any of its stereoisomeric forms or a mixture of stereoisomeric forms in any ratio, or a physiologically acceptable salt thereof, for use as a pharmaceutical, in which R is chosen from halogen, $(C_1-C_6)$-alkyl which can be substituted by one or more fluorine atoms, $(C_1-C_6)$-alkoxy which can be substituted by one or more fluorine atoms, NR7R8, cyano, $(C_1-C_6)$-alkylsulfonyl, aminosulfonyl, nitro, $(C_3-C_7)$-cycloalkyl and $(C_6-C_{14})$-aryl, wherein the aryl residue can be substituted by one or more identical or different substituents chosen from halogen, $(C_1-C_6)$-alkyl, $(C_1-C_6)$-alkoxy and trifluoromethyl;

or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R1 is chosen from hydrogen and (C$_1$-C$_6$)-alkyl;
or R and R1 form together a (C$_1$-C$_2$)-alkylene chain if R is attached in ortho-position of the phenyl ring;
R2 is hydrogen;
R3 is chosen from Br, cyano, nitro, —C(=O)—NR9R10, amino, —N(R11)-C(=O)—R12, COOH, (C$_1$-C$_6$)-alkoxycarbonyl and —C(=NR5)-NHR6;
R4 is each time hydrogen;
R5 is chosen from hydrogen, (C$_1$-C$_6$)-alkoxycarbonyloxy and hydroxy;
R6 is hydrogen;
or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R7 and R8 are independently chosen from hydrogen and (C$_1$-C$_6$)-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and (C$_1$-C$_6$)-alkyl;
or R9 and R10 form, together with the nitrogen atom which carries them, a 4-membered to 7-membered, saturated, partially unsaturated or aromatic heterocyclic ring;
R11 is hydrogen;
R12 is chosen from hydrogen and (C$_1$-C$_6$)-alkyl;
or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R13, R14 and R15 are independently chosen from halogen, (C$_1$-C$_6$)-alkyl, (C$_1$-C$_6$)-alkoxy and trifluoromethyl;
n is chosen from 0, 1, 2, 3, 4 and 5;
provided that compounds are excluded in which R1, R2 and R4 are hydrogen, n is 1, R is cyano and R3 is cyano or COOH,
provided that compounds are excluded in which R1 is hydrogen or methyl, R2 and R4 are hydrogen, n is 1, R3 is COOH or (C$_1$-C$_6$)-alkoxycarbonyl and R is Cl,
provided that compounds are excluded in which R1, R2 and R4 are hydrogen and n is 0,
and provided that compounds are excluded in which R1, R2 and R4 are hydrogen, R3 is Br, n is 1 and R is Br, NO$_2$, dimethylamino, amino, methyl, amide or F.
A more preferred embodiment of the present invention relates to a compound of the formula Ia, in any of its stereoisomeric forms or a mixture of stereoisomeric forms in any ratio, or a physiologically acceptable salt thereof, for use as a pharmaceutical, in which
R is chosen from halogen, (C$_1$-C$_6$)-alkyl which can be substituted by one or more fluorine atoms, (C$_1$-C$_6$)-alkoxy which can be substituted by one or more fluorine atoms, NR7R8, cyano, (C$_1$-C$_6$)-alkylsulfonyl, aminosulfonyl, nitro, (C$_3$-C$_7$)-cycloalkyl and (C$_6$-C$_{14}$)-aryl;
or two adjacent R groups form, together with the carbon atoms which carry them, a 4-membered to 7-membered, partially unsaturated or aromatic heterocyclic ring and which can contain one or two ring members chosen from —N(R4)-, —C(=O)— and —O— which can be identical or different;
R1 is chosen from hydrogen and (C$_1$-C$_6$)-alkyl;
or R and R1 form together a (C$_1$-C$_2$)-alkylene chain if R is attached in ortho-position of the phenyl ring;
R2 is hydrogen;
R3 is chosen from Br, cyano, nitro, —C(=O)—NR9R10, amino, —N(R11)-C(=O)—R12, COOH, (C$_1$-C$_6$)-alkoxycarbonyl and —C(=NR5)-NHR6;
R4 is each time hydrogen;
R5 is chosen from hydrogen, (C$_1$-C$_6$)-alkoxycarbonyloxy and hydroxy;
R6 is hydrogen;
or R5 and R6 form, together with the —N=C—NH— group which carries them, a 4-membered to 7-membered, partially unsaturated or aromatic heterocyclic ring and which, in addition to the nitrogen atoms being part of the —N=C—NH— group, can contain one or two further ring members chosen from —C(=O)— and —O—;
R7 and R8 are independently chosen from hydrogen and (C$_1$-C$_6$)-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and (C$_1$-C$_6$)-alkyl;
or R9 and R10 form, together with the nitrogen atom which carries them, a 4-membered to 7-membered, saturated, partially unsaturated or aromatic heterocyclic ring;
R11 is hydrogen;
R12 is chosen from hydrogen and (C$_1$-C$_6$)-alkyl;
or R11 and R12 form, together with the carbonylamino group which carries them, a 4-membered to 7-membered, saturated, partially unsaturated or aromatic heterocyclic ring and which, in addition to the carbonylamino group connecting R11 and R12, can contain one or two further ring members chosen from —N(R4)- and —C(=O)—;
n is chosen from 0, 1, 2, 3, 4 and 5;
provided that compounds are excluded in which R1, R2 and R4 are hydrogen, n is 1, R is cyano and R3 is cyano or COOH,
provided that compounds are excluded in which R1 is hydrogen or methyl, R2 and R4 are hydrogen, n is 1, R3 is COOH or (C$_1$-C$_6$)-alkoxycarbonyl and R is Cl,
provided that compounds are excluded in which R1, R2 and R4 are hydrogen and n is 0,
and provided that compounds are excluded in which R1, R2 and R4 are hydrogen, R3 is Br, n is 1 and R is Br, NO$_2$, dimethylamino, amino, methyl, amide or F.
Another preferred embodiment of the present invention relates to a compound of the formula Ia, in any of its stereoisomeric forms or a mixture of stereoisomeric forms in any ratio, or a physiologically acceptable salt thereof, for use as a pharmaceutical, wherein the compound of the formula Ia is chosen from:
2-(4-fluoro-phenyl)-imidazo[1,2-a]pyridine-6-carboxylic acid methyl ester, 2-(4-bromo-phenyl)-3-methyl-imidazo[1,2-a]pyridine-6-carboxylic acid methyl ester,
3-methyl-2-phenyl-imidazo[1,2-a]pyridine-6-carboxylic acid methyl ester,
2-(2-oxo-1,2,3,4-tetrahydro-quinolin-6-yl)-imidazo[1,2-a]pyridine-6-carboxylic acid methyl ester,
2-(2-fluoro-phenyl)-imidazo[1,2-a]pyridine-6-carboxylic acid methyl ester,
2-pentafluoro-phenyl-imidazo[1,2-a]pyridine-6-carboxylic acid methyl ester,
2-p-tolyl-imidazo[1,2-a]pyridine-6-carboxylic acid methyl ester,
2-(3-nitro-phenyl)-imidazo[1,2-a]pyridine-6-carboxylic acid methyl ester,
2-(4-methoxy-phenyl)-imidazo[1,2-a]pyridine-6-carboxylic acid methyl ester,
2-naphthalen-2-yl-imidazo[1,2-a]pyridine-6-carboxylic acid methyl ester,
2-(4-bromo-phenyl)-imidazo[1,2-a]pyridine-6-carboxylic acid methyl ester,
2-(3-fluoro-phenyl)-imidazo[1,2-a]pyridine-6-carboxylic acid methyl ester,
2-(4-trifluoromethyl-phenyl)-imidazo[1,2-a]pyridine-6-carboxylic acid methyl ester,
2-(4-trifluoromethoxy-phenyl)-imidazo[1,2-a]pyridine-6-carboxylic acid methyl ester,
2-(4-diethylamino-phenyl)-imidazo[1,2-a]pyridine-6-carboxylic acid methyl ester,
2-(4-cyano-phenyl)-imidazo[1,2-a]pyridine-6-carboxylic acid methyl ester,
2-(2-chloro-phenyl)-imidazo[1,2-a]pyridine-6-carboxylic acid methyl ester,
2-(4-bromo-3-sulfamoyl-phenyl)-imidazo[1,2-a]pyridine-6-carboxylic acid methyl ester,
2-(4-fluoro-3-sulfamoyl-phenyl)-imidazo[1,2-a]pyridine-6-carboxylic acid methyl ester,
2-(3-cyano-phenyl)-imidazo[1,2-a]pyridine-6-carboxylic acid methyl ester,
2-(3-bromo-phenyl)-imidazo[1,2-a]pyridine-6-carboxylic acid methyl ester,
2-(2,4-dimethyl-phenyl)-imidazo[1,2-a]pyridine-6-carboxylic acid methyl ester,
2-(3,4-dichloro-phenyl)-imidazo[1,2-a]pyridine-6-carboxylic acid methyl ester,
2-(4-chloro-3-methyl-phenyl)-imidazo[1,2-a]pyridine-6-carboxylic acid methyl ester,
2-(2,4-dichloro-phenyl)-imidazo[1,2-a]pyridine-6-carboxylic acid methyl ester,
2-(4-cyclohexyl-phenyl)-imidazo[1,2-a]pyridine-6-carboxylic acid methyl ester,
2-(4-methanesulfonyl-phenyl)-imidazo[1,2-a]pyridine-6-carboxylic acid methyl ester,
2-(3-chloro-phenyl)-imidazo[1,2-a]pyridine-6-carboxylic acid methyl ester,
2-(3,5-difluoro-phenyl)-imidazo[1,2-a]pyridine-6-carboxylic acid methyl ester,
2-(3-trifluoromethyl-phenyl)-imidazo[1,2-a]pyridine-6-carboxylic acid methyl ester,
2-(2,3-dihydro-benzo[1,4]dioxin-6-yl)-imidazo[1,2-a]pyridine-6-carboxylic acid methyl ester,
2-(2,6-dichloro-4-trifluoromethyl-phenyl)-imidazo[1,2-a]pyridine-6-carboxylic acid methyl ester,
2-(2-nitro-phenyl)-imidazo[1,2-a]pyridine-6-carboxylic acid methyl ester,
2-biphenyl-4-yl-imidazo[1,2-a]pyridine-6-carboxylic acid methyl ester,
2-(4-nitro-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(2-trifluoromethyl-phenyl)-imidazo[1,2-a]pyridine-6-carboxylic acid methyl ester,
11H-indeno[1',2':4,5]imidazo[1,2-a]pyridine-8-carboxylic acid methyl ester,
2-(4-pyrrolidin-1-yl-phenyl)-imidazo[1,2-a]pyridine-6-carboxylic acid methyl ester,
2-(4-amino-phenyl)-imidazo[1,2-a]pyridine-6-carboxylic acid methyl ester,
2-(4-fluoro-phenyl)-imidazo[1,2-a]pyridine-6-carboxylic acid,
2-p-tolyl-imidazo[1,2-a]pyridine-6-carboxylic acid,
2-(4-diethylamino-phenyl)-imidazo[1,2-a]pyridine-6-carboxylic acid,
2-(4-fluoro-phenyl)-imidazo[1,2-a]pyridine-6-carboxylic acid tert-butylamide,
2-(4-fluoro-phenyl)-imidazo[1,2-a]pyridine-6-carboxylic acid amide,
2-(4-fluoro-phenyl)-imidazo[1,2-a]pyridine-6-carboxylic acid dimethylamide,
azetidin-1-yl-[2-(4-fluoro-phenyl)-imidazo[1,2-a]pyridin-6-yl]-methanone,
2-(4-fluoro-phenyl)-imidazo[1,2-a]pyridine-6-carbonitrile,
2-(4-diethylamino-phenyl)-imidazo[1,2-a]pyridine-6-carbonitrile,
2-p-tolyl-imidazo[1,2-a]pyridine-6-carbonitrile,
2-(3-chloro-phenyl)-imidazo[1,2-a]pyridine-6-carbonitrile,
2-(4-fluoro-phenyl)-N-hydroxy-imidazo[1,2-a]pyridine-6-carboxamidine,
N-hydroxy-2-p-tolyl-imidazo[1,2-a]pyridine-6-carboxamidine,
2-(4-diethylamino-phenyl)-N-hydroxy-imidazo[1,2-a]pyridine-6-carboxamidine,
2-(3-chloro-phenyl)-N-hydroxy-imidazo[1,2-a]pyridine-6-carboxamidine,
2-(4-fluoro-phenyl)-N-ethoxycarbonyloxy-imidazo[1,2-a]pyridine-6-carboxamidine,
6-bromo-2-(4-fluoro-phenyl)-imidazo[1,2-a]pyridine,
[4-(6-bromo-imidazo[1,2-a]pyridin-2-yl)-phenyl]-diethylamine,
2-(4-fluoro-phenyl)-6-nitro-imidazo[1,2-a]pyridine,
2-(4-fluoro-phenyl)-imidazo[1,2-a]pyridin-6-ylamine,
N-[2-(4-fluoro-phenyl)-imidazo[1,2-a]pyridin-6-yl]-formamide,
N-[2-(4-fluoro-phenyl)-imidazo[1,2-a]pyridin-6-yl]-acetamide,
3-[2-(4-fluoro-phenyl)-imidazo[1,2-a]pyridin-6-yl]-imidazolidine-2,4-dione,
3-[2-(4-fluoro-phenyl)-imidazo[1,2-a]pyridin-6-yl]-4H-1,2,4-oxadiazol-5-one, and
2-(4-fluoro-phenyl)-imidazo[1,2-a]pyridine-6-carboxamidine.

Another embodiment of the present invention relates to a compound of the formula Ia in any of its stereoisomeric forms or a mixture of stereoisomeric forms in any ratio, or a physiologically acceptable salt thereof, for use as a pharmaceutical, wherein the compound of the formula Ia is a compound of the formula Ib as defined below.

Another subject of the present invention relates to a compound of the formula Ib,

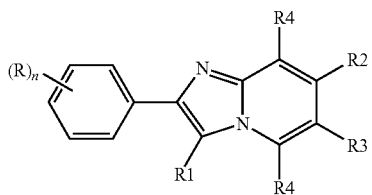

in which
R is chosen from F, Cl, $(C_1-C_6)$-alkyl which can be substituted by one or more fluorine atoms, $(C_1-C_6)$-alkoxy which can be substituted by one or more fluorine atoms, NR7R8, nitro and pentafluorosulfanyl;
or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R1 is chosen from hydrogen and $(C_1-C_6)$-alkyl;
or R and R1 form together a $(C_1-C_2)$-alkylene or $(C_1-C_2)$-alkenylene chain if R is attached in ortho-position of the phenyl ring;
R2 is chosen from hydrogen, hydroxy and $(C_1-C_6)$-alkyl;
R3 is chosen from cyano, —C(=O)—NR9R10, amino, —N(R11)-C(=O)—R12 and —C(=NR5)-NHR6;
R4 is each time independently chosen from hydrogen and $(C_1-C_6)$-alkyl;
R5 is chosen from hydrogen, $(C_1-C_6)$-alkyl, $(C_1-C_6)$-alkylcarbonyl, $(C_1-C_6)$-alkoxycarbonyl, $(C_1-C_6)$-alkoxycarbonyloxy, $(C_1-C_{18})$-alkylcarbonyloxy-$(C_1-C_6)$-alkoxycarbonyl, $(C_6-C_{14})$-arylcarbonyl, $(C_6-C_{14})$-aryloxycarbonyl, hydroxy, $(C_1-C_6)$-alkylcarbonyloxy, $(C_6-C_{14})$-aryl-$(C_1-C_6)$-alkoxycarbonyl, $(C_1-C_6)$-alkylaminocarbonyloxy, di-$((C_1-C_6)$-alkyl)aminocarbonyloxy, $(C_1-C_6)$-alkylaminocarbonyl and di-$((C_1-C_6)$-alkyl)aminocarbonyl, wherein all aryl groups can be substituted by one or more identical or different substituents chosen from halogen, $(C_1-C_6)$-alkyl, $(C_1-C_6)$-alkoxy and trifluoromethyl;
R6 is chosen from hydrogen, cyano, hydroxy, $(C_1-C_6)$-alkoxy and $(C_6-C_{14})$-aryl-$(C_1-C_6)$ alkoxy;
or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R7 and R8 are independently chosen from hydrogen and $(C_1-C_6)$-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and $(C_1-C_6)$-alkyl, with the proviso that at least one of R9 and R10 is not hydrogen;
or R9 and R10 form, together with the nitrogen atom which carries them, a 4-membered to 7-membered, saturated, partially unsaturated or aromatic heterocyclic ring;
R11 is hydrogen;
R12 is hydrogen;
or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, contains one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R13, R14 and R15 are independently chosen from halogen, $(C_1-C_6)$-alkyl, $(C_1-C_6)$-alkoxy and trifluoromethyl;
n is chosen from 1, 2, 3, 4 and 5;
in any of its stereoisomeric forms or a mixture of stereoisomeric forms in any ratio, or a physiologically acceptable salt thereof,
provided that 2-(4-amino-phenyl)-imidazo[1,2-a]pyridin-6-ylamine is excluded.

A preferred embodiment of the present invention relates to a compound of the formula Ib, in which
R is chosen from F, Cl, $(C_1-C_6)$-alkyl and NR7R8;
R1 is hydrogen;
R2 is hydrogen;
R3 is chosen from cyano, —C(=O)—NR9R10, amino, —N(R11)-C(=O)—R12 and —C(=NR5)-NHR6;
R4 is each time hydrogen;
R5 is chosen from hydrogen, $(C_1-C_6)$-alkoxycarbonyloxy and hydroxy;
R6 is hydrogen;
or R5 and R6 form, together with the —N=C—NH— group which carries them, a 4-membered to 7-membered, partially unsaturated or aromatic heterocyclic ring which, in addition to the nitrogen atoms being part of the —N=C—NH— group, can contain one or two further ring members chosen from —C(=O)— and —O—;
R7 and R8 are independently chosen from $(C_1-C_6)$-alkyl;
R9 and R10 are independently chosen from hydrogen and $(C_1-C_6)$-alkyl, with the proviso that at least one of R9 and R10 is not hydrogen;
or R9 and R10 form, together with the nitrogen atom which carries them, a 4-membered to 7-membered, saturated heterocyclic ring;
R11 is hydrogen;
R12 is hydrogen;
or R11 and R12 form, together with the carbonylamino group which carries them, a 4-membered to 7-membered, saturated heterocyclic ring which, in addition to the carbonylamino group connecting R11 and R12, contains one or two further ring members chosen from —N(R4)- and —C(=O)—;
n is 1;
in any of its stereoisomeric forms or a mixture of stereoisomeric forms in any ratio, or a physiologically acceptable salt thereof,
provided that 2-(4-amino-phenyl)-imidazo[1,2-a]pyridin-6-ylamine is excluded.

Another preferred embodiment of the present invention relates to a compound of the formula Ib, wherein the compound of the formula Ib is chosen from:
2-(4-bromo-phenyl)-3-methyl-imidazo[1,2-a]pyridine-6-carboxylic acid methyl ester, 3-methyl-2-phenyl-imidazo[1,2-a]pyridine-6-carboxylic acid methyl ester,
2-(2-oxo-1,2,3,4-tetrahydro-quinolin-6-yl)-imidazo[1,2-a]pyridine-6-carboxylic acid methyl ester,
2-(2-fluoro-phenyl)-imidazo[1,2-a]pyridine-6-carboxylic acid methyl ester,
2-pentafluoro-phenyl-imidazo[1,2-a]pyridine-6-carboxylic acid methyl ester,
2-p-tolyl-imidazo[1,2-a]pyridine-6-carboxylic acid methyl ester,
2-naphthalen-2-yl-imidazo[1,2-a]pyridine-6-carboxylic acid methyl ester,
2-(3-fluoro-phenyl)-imidazo[1,2-a]pyridine-6-carboxylic acid methyl ester,
2-(4-trifluoromethyl-phenyl)-imidazo[1,2-a]pyridine-6-carboxylic acid methyl ester,
2-(4-trifluoromethoxy-phenyl)-imidazo[1,2-a]pyridine-6-carboxylic acid methyl ester,
2-(4-diethylamino-phenyl)-imidazo[1,2-a]pyridine-6-carboxylic acid methyl ester,
2-(4-cyano-phenyl)-imidazo[1,2-a]pyridine-6-carboxylic acid methyl ester,
2-(2-chloro-phenyl)-imidazo[1,2-a]pyridine-6-carboxylic acid methyl ester,
2-(4-bromo-3-sulfamoyl-phenyl)-imidazo[1,2-a]pyridine-6-carboxylic acid methyl ester,
2-(4-fluoro-3-sulfamoyl-phenyl)-imidazo[1,2-a]pyridine-6-carboxylic acid methyl ester,
2-(3-cyano-phenyl)-imidazo[1,2-a]pyridine-6-carboxylic acid methyl ester,
2-(3-bromo-phenyl)-imidazo[1,2-a]pyridine-6-carboxylic acid methyl ester,
2-(2,4-dimethyl-phenyl)-imidazo[1,2-a]pyridine-6-carboxylic acid methyl ester,
2-(3,4-dichloro-phenyl)-imidazo[1,2-a]pyridine-6-carboxylic acid methyl ester,
2-(4-chloro-3-methyl-phenyl)-imidazo[1,2-a]pyridine-6-carboxylic acid methyl ester,
2-(2,4-dichloro-phenyl)-imidazo[1,2-a]pyridine-6-carboxylic acid methyl ester,
2-(3-chloro-phenyl)-imidazo[1,2-a]pyridine-6-carboxylic acid methyl ester,
2-(3,5-difluoro-phenyl)-imidazo[1,2-a]pyridine-6-carboxylic acid methyl ester,
2-(3-trifluoromethyl-phenyl)-imidazo[1,2-a]pyridine-6-carboxylic acid methyl ester,
2-(2,3-dihydro-benzo[1,4]dioxin-6-yl)-imidazo[1,2-a]pyridine-6-carboxylic acid methyl ester,
2-(2,6-dichloro-4-trifluoromethyl-phenyl)-imidazo[1,2-a]pyridine-6-carboxylic acid methyl ester,
2-(2-nitro-phenyl)-imidazo[1,2-a]pyridine-6-carboxylic acid methyl ester,
2-biphenyl-4-yl-imidazo[1,2-a]pyridine-6-carboxylic acid methyl ester,
2-(4-nitro-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(2-trifluoromethyl-phenyl)-imidazo[1,2-a]pyridine-6-carboxylic acid methyl ester,
11H-indeno[1',2':4,5]imidazo[1,2-a]pyridine-8-carboxylic acid methyl ester,
2-(4-pyrrolidin-1-yl-phenyl)-imidazo[1,2-a]pyridine-6-carboxylic acid methyl ester,
2-p-tolyl-imidazo[1,2-a]pyridine-6-carboxylic acid,
2-(4-diethylamino-phenyl)-imidazo[1,2-a]pyridine-6-carboxylic acid,
2-(4-fluoro-phenyl)-imidazo[1,2-a]pyridine-6-carboxylic acid tert-butylamide,
2-(4-fluoro-phenyl)-imidazo[1,2-a]pyridine-6-carboxylic acid dimethylamide,
azetidin-1-yl-[2-(4-fluoro-phenyl)-imidazo[1,2-a]pyridin-6-yl]-methanone,
2-(4-fluoro-phenyl)-imidazo[1,2-a]pyridine-6-carbonitrile,
2-(4-diethylamino-phenyl)-imidazo[1,2-a]pyridine-6-carbonitrile,
2-p-tolyl-imidazo[1,2-a]pyridine-6-carbonitrile,
2-(3-chloro-phenyl)-imidazo[1,2-a]pyridine-6-carbonitrile,
2-(4-fluoro-phenyl)-N-hydroxy-imidazo[1,2-a]pyridine-6-carboxamidine,
N-hydroxy-2-p-tolyl-imidazo[1,2-a]pyridine-6-carboxamidine, 2-(4-diethylamino-phenyl)-N-hydroxy-imidazo[1,2-a]pyridine-6-carboxamidine,
2-(3-chloro-phenyl)-N-hydroxy-imidazo[1,2-a]pyridine-6-carboxamidine,
2-(4-fluoro-phenyl)-N-ethoxycarbonyloxy-imidazo[1,2-a]pyridine-6-carboxamidine, 6-bromo-2-(4-fluoro-phenyl)-imidazo[1,2-a]pyridine,
[4-(6-bromo-imidazo[1,2-a]pyridin-2-yl)phenyl]-diethyl-amine,
2-(4-fluoro-phenyl)-imidazo[1,2-a]pyridin-6-ylamine,
N-[2-(4-fluoro-phenyl)-imidazo[1,2-a]pyridin-6-yl]-formamide,
3-[2-(4-fluoro-phenyl)-imidazo[1,2-a]pyridin-6-yl]-imidazolidine-2,4-dione,
3-[2-(4-fluoro-phenyl)-imidazo[1,2-a]pyridin-6-yl]-4H-1,2,4-oxadiazol-5-one,
2-(4-fluoro-phenyl)-imidazo[1,2-a]pyridine-6-carboxamidine,
in any of its stereoisomeric forms or a mixture of stereoisomeric forms in any ratio, or a physiologically acceptable salt thereof.

If in the compounds of the formulae I, Ia and Ib any groups, substituents, ring members, numbers or other features such as, for example, R, R4, alkyl groups etc. occur several times, they can all independently of one another have any of the indicated meanings and can in each case be identical or different from one another. In a dialkylamino group, for example, the alkyl groups can be identical or different. The compounds of the formula Ia encompass the compounds of the formula Ib. The compounds of the formula I encompass the compounds of the formula Ib and Ia.

Alkyl residues can be linear, i.e. straight-chain, or branched, acyclic or cyclic. This also applies when they are part of other groups, for example alkoxy groups (=alkyloxy groups, i.e. alkyl-O— groups), alkylmercapto groups (=alkyl-S— groups), alkoxycarbonyl groups or alkyl-substituted amino groups, or when they are substituted. In one embodiment of the invention alkyl groups are linear or branched acyclic alkyl groups. Examples of alkyl groups are methyl, ethyl, propyl, butyl, pentyl, hexyl, the n-isomers of these groups, isopropyl, isobutyl, isopentyl, sec-butyl, tert-butyl, neopentyl or 3,3-dimethylbutyl. In one embodiment of the invention, a $(C_1-C_{18})$-alkyl group is a $(C_1-C_6)$-alkyl group. Substituted alkyl groups can be substituted by one or more, for example one, two, three, four or five, identical or different substituents, for example F, which can be located in any desired positions.

As far as applicable, the preceding explanations regarding alkyl groups apply correspondingly to divalent alkyl groups, i.e. alkanediyl groups and alkylene groups, such as methylene ($CH_2$) or ethylene (—$CH_2$—$CH_2$—), as well as to unsaturated divalent alkyl groups comprising a double bond, i.e. alkenediyl groups or alkenylene groups, such as ethenylene (—CH=CH—).

Examples of cycloalkyl groups are cyclopropyl, cyclobutyl, cyclopentyl, cyclohexyl and cycloheptyl. Substituted cycloalkyl groups can be substituted by one or more, for example one, two, three, four or five, identical or different substituents which can be located in any desired positions.

Examples of ($C_6$-$C_{14}$)-aryl residues are phenyl and naphthalenyl. If a ($C_6$-$C_{14}$)-aryl residue, for example phenyl or naphthyl, which can be unsubstituted or substituted, is substituted by one or more substituents, in general it can carry one, two, three, four or five identical or different substituents, for example one or two substitutents. The substituents can be located in any desired positions. This likewise applies to ($C_6$-$C_{14}$)-aryl radicals in groups such as, for example, ($C_6$-$C_{14}$)-arylcarbonyl, ($C_6$-$C_{14}$)-aryloxycarbonyl or ($C_6$-$C_{14}$)-aryl-($C_1$-$C_6$)-alkoxycarbonyl. In monosubstituted phenyl groups the substituent can be located in the 2-position, the 3-position or the 4-position. In a disubstituted phenyl group the substituents can be located in 2,3-position, 2,4-position, 2,5-position, 2,6-position, 3,4-position or 3,5-position. In trisubstituted phenyl groups the substituents can be located in 2,3,4-position, 2,3,5-position, 2,3,6-position, 2,4,5-position, 2,4,6-position or 3,4,5-position. Naphthalenyl (=naphthyl) can be naphthalen-1-yl (1-naphthyl) or naphthalen-2-yl (2-naphthyl). In monosubstituted naphthalen-1-yl groups the substituent can be located in the 2-, 3-, 4-, 5-, 6-, 7-, or 8-position, in monosubstituted naphthalen-2-yl groups the substituent can be located in the 1-, 3-, 4-, 5-, 6-, 7-, or 8-position. In disubstituted naphthalenyl groups the substituents can likewise occur in any desired positions in the ring via which the naphthalenyl group is bonded, and/or in the other ring.

The ring which can be formed by two adjacent R groups together with the carbon atoms which carry them, can be 4-membered, 5-membered, 6-membered or 7-membered, for example 6-membered, and can be partially unsaturated or aromatic, and contains, for example, one, two or three double bonds within the ring, provided the respective ring system is known in the art to be stable and suitable as a subgroup in a drug substance. The ring which can be formed by two adjacent R groups together with the carbon atoms which carry them, can contain one or two further ring members chosen from =N—, —N(R4)-, —C(=O)—, —O—, —S—, —S(O)— and —S(O)$_2$—, for example —N(R4)-, —C(=O)— and —O—, which can be identical or different, with the proviso that two ring members from the series —O—, —S—, —S(O)—, —S(O)$_2$-cannot be present in adjacent ring positions and provided the respective ring system is known in the art to be stable and suitable as a subgroup in a drug substance. The ring which can be formed by two adjacent R groups together with the carbon atoms which carry them, can be substituted by one or more identical or different substituents R13. Examples of the bicyclic ring systems formed by two adjacent R groups together with the anellated phenyl ring which carries the two R groups are: indane, indene, indole, dihydro-indole, isoindole, dihydro-isoindole, isoindolone, indolone, naphthalene, dihydro-naphthalene, tetrahydro-naphthalene, chromane, dihydro-benzodioxine, benzodioxine, quinoline, dihydro-quinoline, tetrahydro-quinoline, isoquinoline, dihydro-isoquinoline, tetrahydro-isoquinoline, dihydro-quinolinone, dihydro-isoquinolinone, quinazoline, dihydro-quinazoline, tetrahydro-quinazoline or dihydro-quinazolinone, for example naphthalene, dihydro-benzodioxine or dihydro-quinolinone.

The heterocyclic ring which can be formed by R5 and R6 together with the —N=C—NH— group which carries them, can be 4-membered, 5-membered, 6-membered or 7-membered, for example 5-membered, and can be partially unsaturated or aromatic, in particular partially unsaturated, and contains, for example, one, two or three double bonds within the ring, provided the respective ring system is known in the art to be stable and suitable as a subgroup in a drug substance. The heterocyclic ring which can be formed by R5 and R6 together with the —N=C—NH— group which carries them, can contain, in addition to the nitrogen atoms being part of the —N=C—NH— group, one or two further ring members chosen from =N—, —N(R4)-, —C(=O)—, —O—, —S—, —S(O)— and —S(O)$_2$—, for example —C(=O)— and —O—, which can be identical or different, with the proviso that two ring members from the series —O—, —S—, —S(O)—, —S(O)$_2$— cannot be present in adjacent ring positions and provided the respective ring system is known in the art to be stable and suitable as a subgroup in a drug substance. The heterocyclic ring which can be formed by R5 and R6 together with the —N=C—NH— group which carries them, can be substituted by one or more identical or different substituents R14. Examples of heterocyclic rings formed by R5 and R6 together with the —N=C—NH— group which carries them, are: imidazole, dihydro-imidazole, pyrimidine, dihydro-pyrimidine, tetrahydro-pyrimidine, diazepine, dihydro-diazepine, tetrahydro-diazepine, diazet-one, oxadiazole, dihydro-oxadiazole, oxadiazol-one, thiadiazole, dihydro-thiadiazole, thiadiazol-one, triazole, dihydro-triazole, dihydro-triazol-one, dihydro-dioxo-thiadiazole, dihydro-oxo-thiadiazole, dioxo-thiadiazole, dihydro-tetrazole, tetrazole, tetrahydro-triazine, dihydro-triazine, triazine, tetrahydro-tetrazine, dihydro-tetrazine, tetrazine, dihydro-oxadiazine, dioxadiazine, oxadiazine, dihydro-thiadiazine, dithiadiazine, thiadiazine, dihydro-oxadiazin-one, oxadiazin-one, pyrimidine-dione, tetrahydro-oxadiazepine, dihydro-oxadiazepine, oxadiazepine, tetrahydro-thiadiazepine, dihydro-thiadiazepine, thiadiazepine, tetrahydro-triazepine, dihydro-triazepine or triazepine, for example oxadiazole.

The heterocyclic ring which can be formed by R7 and R8 together with the nitrogen atom which carries them, can be 4-membered, 5-membered, 6-membered or 7-membered, for example 5-membered, and can be saturated, partially unsaturated or aromatic, in particular saturated, and can contain, for example, one, two or three double bonds within the ring, provided the respective ring system is known in the art to be stable and suitable as a subgroup in a drug substance. Examples of heterocyclic rings formed by R7 and R8 together with the nitrogen atom which carries them, are: azetidine, pyrrolidine, piperidine, azepane, dihydro-azete, azete, dihydro-pyrrole, pyrrole, tetrahydro-pyridine, dihydro-pyridine, pyridine, tetrahydro-azepine, dihydro-azepine, azepine, preferably azetidine, pyrrolidine, piperidine or azepane, for example pyrrolidine.

The heterocyclic ring which can be formed by R9 and R10 together with the nitrogen atom which carries them, can be 4-membered, 5-membered, 6-membered or 7-membered, for example 4-membered, and can be saturated, partially unsaturated or aromatic, in particular saturated, and can contain, for example, one, two or three double bonds within the ring, provided the respective ring system is known in the art to be stable and suitable as a subgroup in a drug substance. Examples of heterocyclic rings formed by R9 and R10 together with the nitrogen atom which carries them, are: azetidine, pyrrolidine, piperidine, azepane, dihydro-azete, azete, dihydro-pyrrole, pyrrole, tetrahydro-pyridine, dihydro-pyridine, pyridine, tetrahydro-azepine, dihydro-azepine, azepine, preferably azetidine, pyrrolidine, piperidine or azepane, for example azetidine.

The heterocyclic ring which can be formed by R11 and R12 together with the carbonylamino group which carries them, can be 4-membered, 5-membered, 6-membered or 7-membered, for example 5-membered, and can be saturated, partially unsaturated or aromatic, in particular saturated, and can contain, for example, one, two or three double bonds within the ring, provided the respective ring system is known in the art to be stable and suitable as a subgroup in a drug substance. The heterocyclic ring which can be formed by R11 and R12 together with the carbonylamino group which carries them, can contain, in addition to the nitrogen atom and the carbonyl group being part of the carbonylamino group, one or two further ring members chosen from =N—, —N(R4)-, —C(=O)—, —O—, —S—, —S(O)— and —S(O)$_2$—, for example —C(=O)— and —N(R4)-, which can be identical or different, with the proviso that two ring members from the series —O—, —S—, —S(O)—, —S(O)$_2$— cannot be present in adjacent ring positions and provided the respective ring system is known in the art to be stable and suitable as a subgroup in a drug substance. The heterocyclic ring which can be formed by R11 and R12 together with the carbonylamino group which carries them, can be substituted by one or more identical or different substituents R15. Examples of heterocyclic rings formed by R11 and R12 together with the carbonylamino group which carries them, are: imidazole, dihydro-imidazole, pyrimidine, dihydro-pyrimidine, tetrahydro-pyrimidine, diazepine, dihydro-diazepine, tetrahydro-diazepine, diazet-one, oxadiazole, dihydro-oxadiazole, oxadiazol-one, thiadiazole, dihydro-thiadiazole, thiadiazol-one, imidazolidin-one, imidazolidine-dione, triazole, dihydro-triazole, dihydro-triazol-one, dihydro-dioxo-thiadiazole, dihydro-oxo-thiadiazole, dioxo-thiadiazole, dihydro-tetrazole, tetrazole, tetrahydro-triazine, dihydro-triazine, triazine, tetrahydro-tetrazine, dihydro-tetrazine, tetrazine, dihydro-oxadiazine, dioxadiazine, oxadiazine, dihydro-thiadiazine, dithiadiazine, thiadiazine, dihydro-oxadiazin-one, oxadiazin-one, pyrimidine-dione, tetrahydro-oxadiazepine, dihydro-oxadiazepine, oxadiazepine, tetrahydro-thiadiazepine, dihydro-thiadiazepine, thiadiazepine, tetrahydro-triazepine, dihydro-triazepine or triazepine, for example imidazolidine-2,4-dione.

Halogen is fluorine, chlorine, bromine or iodine, preferably fluorine, chlorine or bromine, for example fluorine.

An oxo group, when bonded to a carbon atom, replaces two hydrogen atoms on a carbon atom of the parent system. Thus, if a CH$_2$ group is substituted by oxo, i.e. by a doubly bonded oxygen atom, it becomes a C(=O) group. Evidently, an oxo group cannot occur as a substituent on a carbon atom in an aromatic ring.

The present invention includes all stereoisomeric forms of the compounds of the formulae I, Ia and Ib and their salts. With respect to each chiral center, independently of any other chiral center, the compounds of the formulae I, Ia and Ib can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings, the invention includes both the E form and Z form, or the cis form and the trans form, as well as mixtures of these forms in all ratios. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally a derivatization can be carried out before a separation of stereoisomers. The separation of a mixture of stereoisomers can be carried out at the stage of the compound of the formulae I, Ia or Ib or at the stage of a starting material or an intermediate during the synthesis.

The present invention also includes all tautomeric forms of the compounds of the formulae I, Ia and Ib and their salts. For example, the invention includes the tautomeric forms of the group C(=NR5)-NHR6:

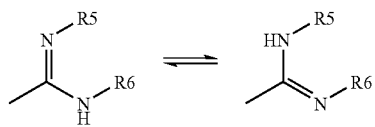

In case the compounds of the formulae I, Ia and Ib contain one or more acidic and/or basic groups, i.e. salt-forming groups, the invention also comprises their corresponding physiologically or toxicologically acceptable salts, i.e. non-toxic salts, in particular their pharmaceutically acceptable salts. Thus, the compounds of the formulae I, Ia and Ib which contain an acidic group can be present on such groups, and can be used according to the invention, for example, as alkali metal salts, alkaline earth metal salts or as ammonium salts. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formulae I, Ia and Ib which contain a basic group, i.e. a group which can be protonated, can be present on such groups, and can be used according to the invention, for example, in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, nicotinic acid, isonicotinic acid, citric acid, adipic acid, and other acids known to the person skilled in the art. If the compounds of the formulae I, Ia and Ib simultaneously contain acidic and basic groups in the molecule, the invention also includes, in addition to the salt forms mentioned, inner salts or betaines or zwitterions. The salts of the compounds of the formulae I, Ia and Ib can be obtained by customary methods which are known to the person skilled in the art like, for example, by contacting the compound of the formulae I, Ia and Ib or Ia with an organic or inorganic acid or base in a solvent or diluent, or by anion exchange or cation exchange from another salt. The present invention also includes all salts of the compounds of the formulae I, Ia and Ib which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formulae I, Ia and Ib, for example hydrates or adducts with alcohols, active metabolites of the compounds of the formulae I, Ia and Ib, and also prodrugs and derivatives of the compounds of the formulae I, Ia and Ib which in vitro may not necessarily exhibit pharmacological activity but which in vivo are converted into pharmacologically active compounds, for example esters or amides of carboxylic acid groups.

In one embodiment of the invention the group R in the compounds of the formulae I and Ia is chosen from halogen, $(C_1-C_6)$-alkyl which can be substituted by one or more fluorine atoms, $(C_1-C_6)$-alkoxy which can be substituted by one or more fluorine atoms, NR7R8, cyano, $(C_1-C_6)$-alkylsulfonyl, aminosulfonyl, nitro, $(C_3-C_7)$-cycloalkyl and $(C_6-C_{14})$-aryl, wherein the aryl residue can be substituted by one or more identical or different substituents chosen from halogen, $(C_1-C_6)$-alkyl, $(C_1-C_6)$-alkoxy and trifluoromethyl, or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions. In another embodiment, the group R in the compounds of the formulae I and Ia is chosen from halogen, for example F, Cl or Br, $(C_1-C_6)$-alkyl which can be substituted by one or more fluorine atoms, for example methyl or trifluoromethyl, $(C_1-C_6)$-alkoxy which can be substituted by one or more fluorine atoms, for example methoxy or trifluoromethoxy, NR7R8, cyano, $(C_1-C_6)$-alkylsulfonyl, for example methylsulfonyl, aminosulfonyl, nitro, $(C_3-C_7)$-cycloalkyl, for example cyclohexyl, and $(C_6-C_{14})$-aryl, for example phenyl, or two adjacent R groups form, together with the carbon atoms which carry them, a 4-membered to 7-membered, preferably 6-membered, partially unsaturated or aromatic heterocyclic ring and which can contain one or two ring members chosen from —N(R4)-, —C(=O)— and —O— which can be identical or different. For example, the ring formed by the two adjacent R groups together with the carbon atoms which carry them, can be a benzene, dihydro-dioxane or dihydro-pyridine ring. In another embodiment the group R in the compounds of the formulae I and Ia is chosen from F, Cl, Br, I, methyl, ethyl, trifluoromethyl, methoxy, ethoxy, trifluoromethoxy, amino, dimethylamino, diethylamino, azetidinyl, pyrrolidinyl, piperidinyl, cyano, methylsulfonyl, aminosulfonyl, nitro, cyclopentyl, cyclohexyl, naphthyl and phenyl, for example from F, Cl, Br, methyl, trifluoromethyl, methoxy, trifluoromethoxy, amino, diethylamino, pyrrolidinyl, cyano, methylsulfonyl, aminosulfonyl, nitro, cyclohexyl and phenyl. In another embodiment two adjacent groups R in the compounds of the formulae I or Ia form, together with the annelated phenyl ring which carries the two groups R, a bicyclic ring system, for example an indane, indene, indole, dihydro-indole, isoindole, dihydro-isoindole, isoindolone, indolone, naphthalene, dihydro-naphthalene, tetrahydro-naphthalene, chromane, dihydro-benzodioxine, benzodioxine, quinoline, dihydro-quinoline, tetrahydro-quinoline, isoquinoline, dihydro-isoquinoline, tetrahydro-isoquinoline, dihydro-quinolinone, dihydro-isoquinolinone, quinazoline, dihydro-quinazoline, tetrahydro-quinazoline or dihydro-quinazolinone ring, preferably a naphthalene, dihydro-benzodioxine or dihydro-quinolinone ring. In one embodiment of the invention the group R in the compounds of the formula Ib is chosen from F, Cl, $(C_1-C_6)$-alkyl and NR7R8, preferably from F, Cl, methyl, ethyl, amino, dimethylamino and diethylamino, for example from F, Cl and diethylamino. In one embodiment of the invention the group R in the compounds of the formulae I and Ia, in which the group R1 is hydrogen, cannot be an unsubstituted or substituted $(C_6-C_{14})$-aryl group, in particular not an unsubstituted or substituted phenyl group, which is located in the 4-position of the phenyl ring depicted in the formulae I and Ia, if any one or more of positions 2, 3, 5 and 6 in the phenyl ring depicted in the formulae I and Ia carry fluorine atoms as sole further substituents or if no further groups R are present in the phenyl ring depicted in the formulae I and Ia. I.e., in this latter embodiment the phenyl group depicted in the formulae I and Ia, together with the groups (R)$_n$, cannot be a 4-(($C_6-C_{14}$)-aryl)-phenyl group, in particular not a biphenyl-4-yl group, in which the phenyl group bonded to the bicyclic heterocycle does not carry any further substituents or carries one or more fluorine atoms as sole further substituents, wherein the $(C_6-C_{14})$-aryl group and the terminal phenyl group of the biphenyl-4-yl group are unsubstituted or substituted. In another embodiment, the group R is defined as indicated in the definitions of the compounds of the formulae I and Ia except that R cannot be unsubstituted or substituted $(C_6-C_{14})$-aryl.

In one embodiment of the invention, the group R1 in the compounds of the formulae I, Ia and Ib is chosen from hydrogen and $(C_1-C_4)$-alkyl, in another embodiment from hydrogen and methyl. In the compounds of the formulae I and Ia the group R1 is preferably chosen from hydrogen and methyl, and in the compounds of the formula Ib the group R1 is preferably hydrogen. In one embodiment of the invention the group R1 in the compounds of the formulae I, Ia and b is hydrogen. In another embodiment, R1 and R in the compounds of the formulae I and Ia form together a $(C_1-C_2)$-alkylene chain, for example a methylene chain $(CH_2)$, if R is attached in ortho-position of the phenyl ring.

In one embodiment the group R2 in the compounds of the formulae I, Ia and Ib is chosen from hydrogen, hydroxy and methyl, in another embodiment from hydrogen and methyl, and in another embodiment R2 is hydrogen.

In one embodiment R3 in the compounds of the formulae I and Ia is chosen from Br, cyano, nitro, —C(=O)—NR9R10, amino, —N(R11)-C(=O)—R12, COOH, $(C_1-C_6)$-alkoxycarbonyl and —C(=NR5)-NHR6; in another embodiment from Br, cyano, nitro, —C(=O)—NR9R10, amino, —N(R11)-C(=O)—R12, COOH, methoxycarbonyl, ethoxycarbonyl, and —C(=NR5)-NHR6, in another embodiment from Br, cyano, nitro, —C(=O)—NR9R10, amino, —N(R11)-C(=O)—R12, COOH, methoxycarbonyl or —C(=NR5)-NHR6. In one embodiment of the invention the group R3 in the compounds of the formula Ib is chosen from cyano, —C(=O)—NR9R10, amino, —N(R11)-C(=O)—R12 and —C(=NR5)-NHR6.

In one embodiment of the invention the groups R4 in the compounds of the formulae I, Ia and Ib are independently chosen from hydrogen and methyl, in another embodiment R4 is defined as hydrogen.

In one embodiment the group R5 in the compounds of the formulae I, Ia and Ib is chosen from hydrogen, $(C_1-C_6)$-alkoxycarbonyloxy and hydroxy; for example from hydrogen, ethoxycarbonyloxy, methoxycarbonyloxy and hydroxy, in particular from hydrogen, ethoxycarbonyloxy and hydroxy. In another embodiment R5 is hydrogen.

In one embodiment of the invention the group R6 in the compounds of the formulae I, Ia and Ib is defined as hydrogen.

In one embodiment the groups R5 and R6 in the compounds of the formulae I, Ia and Ib form, together with the —N═C—NH— group which carries them, a 4-membered to 7-membered, for example a 5-membered or 6-membered, partially unsaturated or aromatic heterocyclic ring which can be substituted by one or more identical or different substituents R14 and which, in addition to the nitrogen atoms being part of the —N═C—NH— group, can contain one or two further ring members chosen from ═N—, —N(R4)-, —C(═O)—, —O—, —S—, —S(O)— and —S(O)$_2$—, for example —C(═O)— and —O—, which can be identical or different, with the proviso that two ring members from the series —O—, —S—, —S(O)—, —S(O)$_2$— cannot be present in adjacent ring positions. For example, R5 and R6 in the compounds of the formulae I, Ia and Ib can form, together with the —N═C—NH— group which carries them, a ring such as imidazole, dihydro-imidazole, pyrimidine, dihydro-pyrimidine, tetrahydro-pyrimidine, diazepine, dihydro-diazepine, tetrahydro-diazepine, diazet-one, oxadiazole, dihydro-oxadiazole, oxadiazol-one, thiadiazole, dihydro-thiadiazole, thiadiazol-one, triazole, dihydro-triazole, dihydro-triazol-one, dihydro-dioxo-thiadiazole, dihydro-oxo-thiadiazole, dioxo-thiadiazole, dihydro-tetrazole, tetrazole, tetrahydro-triazine, dihydro-triazine, triazine, tetrahydro-tetrazine, dihydro-tetrazine, tetrazine, dihydro-oxadiazine, dioxadiazine, oxadiazine, dihydro-thiadiazine, dithiadiazine, thiadiazine, dihydro-oxadiazin-one, oxadiazin-one, pyrimidine-dione, tetrahydro-oxadiazepine, dihydro-oxadiazepine, oxadiazepine, tetrahydro-thiadiazepine, dihydro-thiadiazepine, thiadiazepine, tetrahydro-triazepine, dihydro-triazepine or triazepine, for example oxadiazole.

In one embodiment the groups R7 and R8 in compounds of the formulae I, Ia and Ib are independently chosen from hydrogen and (C$_1$-C$_4$)-alkyl, in another embodiment from hydrogen, methyl, ethyl and isopropyl, in another embodiment from (C$_1$-C$_4$)-alkyl, in another embodiment from methyl, ethyl and isopropyl. In one embodiment the groups R7 and R8 in the compounds of the formulae I and Ia are chosen from hydrogen, methyl and ethyl, in another embodiment from hydrogen and ethyl. In another embodiment the groups R7 and R8 in the compounds of the formula Ib are ethyl.

In another embodiment R7 and R8 in the compounds of the formulae I, Ia and Ib form, together with the nitrogen atom which carries them, a 4-membered to 7-membered, for example 5-membered, saturated, partially unsaturated or aromatic, preferably saturated, heterocyclic ring. For example, R7 and R8 in the compounds of the formulae I and Ia can form, together with the nitrogen atom which carries them, a ring such as azetidine, pyrrolidine, piperidine, azepane, dihydro-azete, azete, dihydro-pyrrole, pyrrole, tetrahydro-pyridine, dihydro-pyridine, pyridine, tetrahydro-azepine, dihydro-azepine, azepine, preferably azetidine, pyrrolidine, piperidine or azepane, for example pyrrolidine.

In one embodiment the groups R9 and R10 in compounds of the formulae I and Ia are independently chosen from hydrogen and (C$_1$-C$_4$)-alkyl; in another embodiment from hydrogen, methyl, ethyl, isopropyl and tert-butyl, in another embodiment from hydrogen, methyl and tert-butyl. In one embodiment the groups R9 and R10 in the compounds of the formula Ib are independently chosen from hydrogen and (C$_1$-C$_4$)-alkyl, with the proviso that at least one of the groups R9 and R10 is not hydrogen. in another embodiment R9 and R10 in the compounds of the formula Ib are independently chosen from hydrogen, methyl, ethyl, isopropyl and tert-butyl, for example from hydrogen, methyl and tert-butyl, with the proviso that at least one of the groups R9 and R10 is not hydrogen.

In another embodiment the groups R9 and R10 in the compounds of the formulae I, Ia and Ib form, together with the nitrogen atom which carries them, a 4-membered to 7-membered, for example 4-membered, saturated, partially unsaturated or aromatic, preferably saturated, heterocyclic ring. For example, R9 and R10 in the compounds of the formulae I, Ia and Ib can form, together with the nitrogen atom which carries them, a ring such as azetidine, pyrrolidine, piperidine, azepane, dihydro-azete, azete, dihydro-pyrrole, pyrrole, tetrahydro-pyridine, dihydro-pyridine, pyridine, tetrahydro-azepine, dihydro-azepine, azepine, preferably azetidine, pyrrolidine, piperidine or azepane, for example azetidine.

In one embodiment of the invention the group R11 in the compounds of the formulae I, Ia and Ib is hydrogen.

In one embodiment the group R12 in the compounds of the formulae I and Ia is chosen from hydrogen and (C$_1$-C$_4$)-alkyl, in another embodiment from hydrogen, methyl and ethyl, in another embodiment from hydrogen and methyl, and in another embodiment R12 is hydrogen. In one embodiment the group R12 in the compounds of the formula Ib is hydrogen.

In another embodiment the groups R11 and R12 in the compounds of the formulae I, Ia and Ib form, together with the carbonylamino group which carries them, a 4-membered to 7-membered, for example 5-membered, saturated, partially unsaturated or aromatic, preferably saturated, heterocyclic ring which can be substituted by one or more identical or different substituents R15 and which, in addition to the carbonylamino group connecting R11 and R12, can contain one or two further ring members chosen from ═N—, —N(R4)-, —C(═O)—, —O—, —S—, —S(O)— and —S(O)$_2$—, for example —N(R4)- or —C(═O)—, which can be identical or different, with the proviso that two ring members from the series —O—, —S—, —S(O)—, —S(O)$_2$— cannot be present in adjacent ring positions. For example, R11 and R12 in the compounds of the formulae I, Ia and Ib can form, together with the carbonylamino group which carries them, a ring system such as imidazole, dihydro-imidazole, pyrimidine, dihydro-pyrimidine, tetrahydro-pyrimidine, diazepine, dihydro-diazepine, tetrahydro-diazepine, diazete, oxadiazole, dihydro-oxadiazole, thiadiazole, dihydro-thiadiazole, imidazolidine, triazole, dihydro-triazole, dihydro-dioxo-thiadiazole, dihydro-oxo-thiadiazole, dioxo-thiadiazole, dihydro-tetrazole, tetrazole, tetrahydro-triazine, dihydro-triazine, triazine, tetrahydro-tetrazine, dihydro-tetrazine, tetrazine, dihydro-oxadiazine, dioxadiazine, oxadiazine, dihydro-thiadiazine, dithiadiazine, thiadiazine, tetrahydro-oxadiazepine, dihydro-oxadiazepine, oxadiazepine, tetrahydro-thiadiazepine, dihydro-thiadiazepine, thiadiazepine, tetrahydro-triazepine, dihydro-triazepine or triazepine carrying at least the oxo group present in the carbonylamino group carrying R11 and R12, and thus a moiety such as diazet-one, oxadiazol-one, thiadiazol-one, imidazolidin-one, imidazolidin-dione, dihydro-triazol-one, dihydro-oxadiazin-one, oxadiazin-one or pyrimidine-dione, for example imidazolidine-2,4-dione.

In one embodiment of the invention the groups R13, R14 and R15 in compounds of the formulae I, Ia and Ib are independently chosen from halogen, (C$_1$-C$_4$)-alkyl, (C$_1$-C$_4$)-alkoxy and trifluoromethyl, in another embodiment from F, Cl, Br, methyl, ethyl, methoxy and trifluoromethyl.

In one embodiment of the invention the number n of the substituents R on the phenyl ring depicted in the formulae I, Ia and Ib is chosen from 0, 1, 2 and 5, in another embodiment from 0, 1 and 2, in another embodiment from 1, 2 and 5, in another embodiment from 1 and 2.

In one embodiment of the invention the group R1 in the compounds of the formulae I and Ia is chosen from H and $(C_1-C_6)$-alkyl or R and R1 form together a $(C_1-C_2)$-alkylene chain if R is attached in ortho-position of the phenyl ring, and the group R3 is defined as $(C_1-C_6)$-alkoxycarbonyl.

In one embodiment of the invention the group R1 in the compounds of the formulae I, Ia and Ib is H and the group R3 is defined as Br, cyano, nitro, —C(=O)—NR9R10, amino, —N(R11)-C(=O)—R12, COOH or —C(=NR5)-NHR6.

In one embodiment of the invention the number n in the compounds of the formulae I and Ia is 0, 1, 2 or 5 and R3 is defined as $(C_1-C_6)$-alkoxycarbonyl.

In one embodiment of the invention the number n in the compounds of the formulae I, Ia and Ib is 1 and R3 is defined as Br, cyano, nitro, —C(=O)—NR9R10, amino, —N(R11)-C(=O)—R12, COOH or —C(=NR5)-NHR6.

In one embodiment of the invention the group R in the compounds of the formulae I and Ia is chosen from F, Cl, $(C_1-C_6)$-alkyl and NR7R8 and R3 is defined as Br.

In one embodiment of the invention the group R in the compounds of the formulae I, Ia and Ib is chosen from F, Cl, $(C_1-C_6)$-alkyl and NR7R8 and R3 is defined a cyano.

In one embodiment of the invention the group R in the compounds of the formulae I and Ia is F and R3 is defined as nitro.

In one embodiment of the invention the group R in the compounds of the formulae I, Ia and Ib is F and R3 is defined as —C(=O)—NR9R10.

In one embodiment of the invention the group R in the compounds of the formulae I, Ia and Ib is F and R3 is defined as amino.

In one embodiment of the invention the group R in the compounds of the formulae I, Ia and Ib is F and R3 is defined as —N(R11)-C(=O)—R12.

In one embodiment of the invention the group R in the compounds of the formulae I and Ia is chosen from F, $(C_1-C_6)$-alkyl and NR7R8 and R3 is defined as COOH.

In one embodiment of the invention the group R in the compounds of the formulae I and Ia is chosen from halogen, $(C_1-C_6)$-alkyl which can be substituted by one or more fluorine atoms, $(C_1-C_6)$-alkoxy which can be substituted by one or more fluorine atoms, NR7R8, cyano, $(C_1-C_6)$-alkylsulfonyl, aminosulfonyl, nitro, $(C_3-C_7)$-cycloalkyl and $(C_6-C_{14})$-aryl, or two adjacent R groups form, together with the carbon atoms which carry them, a 4-membered to 7-membered, partially unsaturated or aromatic heterocyclic ring which can contain one or two ring members chosen from —N(R4)-, —C(=O)— and —O— which can be identical or different, and R3 is defined as $(C_1-C_6)$-alkoxycarbonyl.

In one embodiment of the invention the group R in the compounds of the formulae I, Ia and Ib is chosen from F, Cl, $(C_1-C_6)$-alkyl and NR7R8 and R3 is defined as —C(=NR5)-NHR6.

The compounds according to the formulae I, Ia and Ib and their precursors can be prepared according to methods published in the literature or, respectively, analogous methods. For example, the compounds of the formula I, Ia and Ib can be prepared by reacting a compound of the formula II with a compound of the formula III:

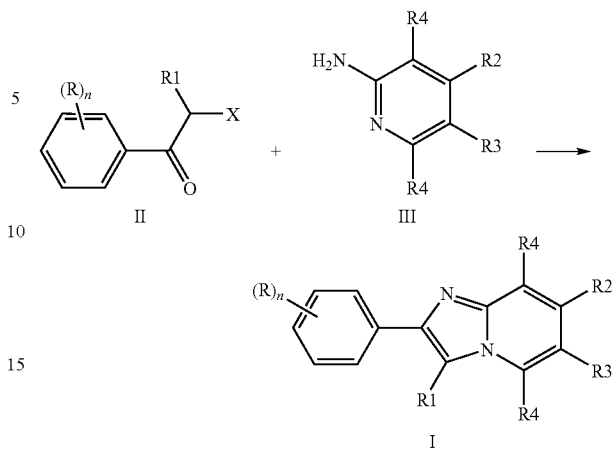

In the compounds of the formulae II and III the variables R, R1, R2, R3, R4 and n are defined as in the compounds of the formula I. The reaction of the compounds of the formulae II and III can be carried out in an inert solvent, which can be protic or aprotic and aqueous or non-aqueous, for example hexane, toluene, dichloromethane, dichloroethane, trichloromethane, tetrachloromethane, an ether, for example diethyl ether, tetrahydrofuran (=THF), dioxane, an amide, for example N,N-dimethylformamide (=DMF), an alcohol, for example methanol or ethanol, water or acetonitrile, or a mixture of two or more solvents, including a mixture of water and an organic solvent which is miscible or immiscible with water. Alternatively, the reaction can be carries out under solvent-free conditions. The reaction can be carried out in the presence of a base or with microwave irradiation. The reaction of the compounds of the formulae II and III can be carried out in a wide temperature range. Usually it is advantageous to perform the reaction at temperatures from about −20° C. to about the boiling point of the solvent used, preferably at from about 0° C. to about 140° C., more preferably at about the boiling point of the solvent. As is usual, the detailed conditions of a specific preparation, including the solvent, the base, the temperature, the order of addition, the molar ratios and other parameters, are routinely chosen by the person skilled in the art in view of the characteristics of the starting compounds and the target compound. Appropriate methods have been published, for example, in P. Sanfilippo et al., Journal of Medicinal Chemistry (1988), 31(11), 2221-7; or G. Trapani et al., Journal of Medicinal Chemistry (1997), 40(19), 3109-3118.

All reactions used in the above-described syntheses of the compounds of the formula I are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid an unwanted course of a reaction or side reactions during the synthesis of a compound, it can generally be necessary or advantageous to temporarily block functional groups by introducing protective groups and deprotect them at a later stage of the synthesis, or introduce functional groups in the form of precursor groups which later are converted into the desired functional groups. As a further example of protecting groups, besides the above-mentioned amino-protecting groups, ester protecting groups of carboxylic acid groups may be mentioned, such as tert-butyl esters which can be deprotected by treatment with trifluoroacetic acid, or benzyl esters which can be deprotected by catalytic hydrogenation. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person. Another type of conversion is starting from compounds of the formula I, where R3 is a carboxylic acid ester group. By standard procedures described in the literature, the ester group can be transferred to an amide group by direct reaction with ammonia or an amine or indirectly via saponification of the ester groups and reaction of the free carboxylic acid with ammonia or an amine. The primary amide obtained with ammonia can be dehydrated to get the corresponding nitrile. Numerous procedures are described in the literature to conduct such types of reactions, for example in D. S. Bose and B. Jayalakshmi, Synthesis (1999), 4-65. Nitriles are easily converted by addition of nitrogen-containing compounds such as amines or hydroxylamines to adducts like amidines or hydroxyamidines. Numerous such procedures are described in the literature, for example in Houben-Weyl, Methoden der Organischen Chemie (Methods of Organic Chemistry), volume XI/2, p 39, Thieme-Verlag, Stuttgart; G. Wagner, P. Richter and Ch. Garbe, Pharmazie (1974), 29, 12-15; Z. Li et al, J. Med. Chem. (2005), 48(20), 6169-6173; or M. D. Bjorklund and M. D. Coburn, J. Het. Chem. (1980), 17(4), 819-21.

If desired, the obtained compounds of the formulae I, Ia and Ib, as well as any intermediate compounds, can be purified by customary purification procedures, for example by recrystallization or chromatography.

The compounds of the formulae I, Ia and Ib are useful pharmacologically active, or pharmaceutically active compounds which modulate the expression of endothelial NO synthase, and more specifically upregulate, or stimulate, the expression, or transcription, of endothelial NO synthase, and which can be employed as pharmaceuticals, or active ingredients of medicaments, for the treatment of various diseases. In the context of the present invention, treatment is understood as comprising both therapy, including alleviation and cure, of diseases and disease symptoms and prevention and prophylaxis of diseases and disease symptoms, such as, for example, the prevention of the appearance of asthmatic disease symptoms or the prevention of myocardial infarction or of myocardial reinfarction in affected patients. The diseases or disease symptoms can be acute or chronic. Diseases which can be treated with the compounds of the formulae I, Ia and Ib include, for example, cardiovascular diseases like stable and unstable angina pectoris, coronary heart disease, coronary artery disease, Prinzmetal angina (spasm), acute coronary syndrome, cardiac insufficiency, heart failure, myocardial infarction, stroke, thrombosis, peripheral artery occlusive disease (=PAOD), endothelial dysfunction, atherosclerosis, restenosis, endothel damage after PTCA (=percutaneous transluminal coronary angioplasty), hypertension including essential hypertension, pulmonary hypertension and secondary hypertension (renovascular hypertension, chronic glomerulonephritis), erectile dysfunction, and ventricular arrhythmia. Further, the compounds of the formulae I, Ia and Ib lower the cardiovascular risk of postmenopausal women or after intake of contraceptives. Compounds of the formulae I, Ia and Ib can additionally be used in the treatment, including therapy and prevention, of diabetes and diabetes complications such as nephropathy or retinopathy, angiogenesis, asthma bronchiale, chronic renal failure, cirrhosis of the liver, osteoporosis, restricted memory performance or a restricted ability to learn. Preferred indications are chronic heart failure, stable angina pectoris, coronary heart disease, hypertension, endothelial dysfunction, atherosclerosis and diabetes complications.

The compounds of the formulae I, Ia and Ib can be used in combination with other pharmacologically active compounds or pharmaceuticals, preferably with compounds which are able to enhance the effect of the compounds according to the formulae I, Ia and Ib. Examples of such other compounds include statins; ACE inhibitors; AT1 antagonists; argininase inhibitors; PDE V inhibitors; calcium antagonists; alpha blockers; beta blockers; metimazol and analogous compounds; arginine; tetrahydrobiopterin; vitamins, in particular vitamin C and vitamin B6; niacine.

The compounds of the formulae I, Ia and Ib and their physiologically acceptable salts, optionally in combination with other pharmacologically active compounds, can be administered to animals, preferably to mammals, and in particular to humans, as pharmaceuticals by themselves, in mixtures with one another, or in the form of pharmaceutical compositions. Further subjects of the present invention therefore also are the compounds of the formulae I, Ia and Ib and their physiologically acceptable salts for use as pharmaceuticals, their use as modulating agents, and more specifically as stimulating agents or upregulating agents, of the expression or transcription of endothelial NO synthase, for example in conditions in which an increased expression of said enzyme or an increased NO level or the normalization of a decreased NO level in a patient is desired, and in particular their use in the treatment, including therapy and prevention, of the above-mentioned diseases or syndromes, as well as their use for the preparation or manufacture of medicaments for these purposes. Furthermore, a subject of the present invention are pharmaceutical compositions, or pharmaceutical preparations, which comprise an effective dose of at least one compound of the formulae I or Ia and/or a physiologically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, for example in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formulae I, Ia or Ib and/or its physiologically acceptable salts present in the pharmaceutical compositions normally ranges from about 0.2 to about 800 mg, preferably from about 0.5 to about 500 mg, in particular from about 1 to about 200 mg, per dose, but depending on the type of the pharmaceutical composition it may also be higher. The pharmaceutical compositions usually comprise from about 0.5 to about 90 percent by weight of the compounds of the formulae I or Ia and/or their physiologically acceptable salts. The production of the pharmaceutical compositions can be carried out in a manner known per se. To this end, one or more compounds of the formulae I or Ia and/or their physiologically acceptable salts together with one or more solid or liquid pharmaceutical carrier substances (or vehicles) and/or additives (or auxiliary substances) and, if a combination medicament is desired, other pharmacologically active compounds having therapeutic or prophylactic action are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, starch derivatives, talc, stearic acid or its salts, etc. Soft gelatin capsules and suppositories can comprise, for example, fats, waxes, semisolid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formulae I, Ia and Ib and their physiologically acceptable salts and to use the resulting lyophilisates, for example, for preparing compositions for injection or infusion. Suitable carriers for microcapsules, implants or rods are, for example, copolymers of glycolic acid and lactic acid. Besides the compound or compounds according to the invention and carrier substances, the pharmaceutical compositions can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formulae I, Ia or Ib to be administered and/or of a physiologically acceptable salt thereof depends on the individual case and, as is customary, has to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the use is for the therapy of a acute or chronic disease or prophylactic, or on whether other active compounds are administered in addition to compounds of the formulae I or Ia. In general, a daily dose from about 0.01 mg/kg to about 100 mg/kg, preferably from about 0.1 mg/kg to about 10 mg/kg, in particular from about 0.3 mg/kg to about 5 mg/kg (in each case mg per kg of bodyweight) is appropriate for administration to an adult weighing about 75 kg in order to obtain the desired results. The daily dose can be administered in a single dose or, in particular when larger amounts are administered, divided into several, for example two, three or four individual doses. In some cases, depending on the individual response, it may be necessary to deviate upwards or downwards from the given daily dose.

The compounds of the formulae I, Ia and Ib can also be used for other purposes than those indicated in the foregoing. Non-limiting examples include the use as diagnostics, for example the use in methods for determining the activity of endothelial NO synthase in biological samples, the use as biochemical tools and the use as intermediates for the preparation of further compounds, for example further pharmacologically active compounds.

| List of abbreviations: | |
|---|---|
| DMF | N,N-Dimethylformamide |
| HPLC | High performance liquid chromatography |
| TFA | Trifluoroacetic acid |

EXAMPLES

Example 1

2-(4-Fluoro-phenyl)-imidazo[1,2-a]pyridine-6-carboxylic acid methyl ester

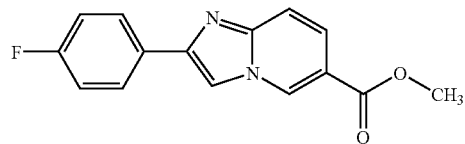 [SMILES: COC(=O)c1ccc2nc(-c3ccc(F)cc3)cn2c1]

2-Bromo-1-(4-fluoro-phenyl)-ethanone (1.135 g, 5.23 mmol) and 6-amino-nicotinic acid methyl ester (795.7 mg, 5.23 mmol) were heated under reflux in 50 ml dioxane for 8.5 hours. After cooling the solid was filtered and dried. Yield: 1.36 g, 96%. MS (mass spectrum): M+H$^+$=271.06.

Example 2

2-(4-Bromo-phenyl)-3-methyl-imidazo[1,2-a]pyridine-6-carboxylic acid methyl ester

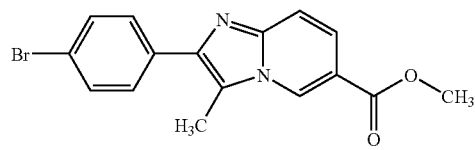

The compound was synthesized analogously to example 1. MS: M+H$^+$=345.03.

Example 3

3-Methyl-2-phenyl-imidazo[1,2-a]pyridine-6-carboxylic acid methyl ester

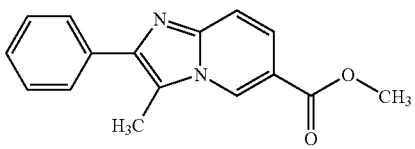 [SMILES: COC(=O)c1ccc2nc(-c3ccccc3)c(C)n2c1]

The compound was synthesized analogously to example 1. MS: M+H$^+$=267.13.

Example 4

2-(2-Oxo-1,2,3,4-tetrahydro-quinolin-6-yl)-imidazo[1,2-a]pyridine-6-carboxylic acid methyl ester

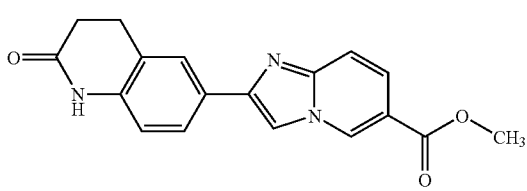 [SMILES: COC(=O)c1ccc2nc(-c3ccc4c(c3)CCC(=O)N4)cn2c1]

The compound was synthesized analogously to example 1.
MS: M+H$^+$=322.15.

Example 5

2-(2-Fluoro-phenyl)-imidazo[1,2-a]pyridine-6-carboxylic acid methyl ester

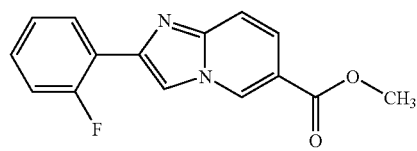

The compound was synthesized analogously to example 1.
MS: M+H$^+$=271.10.

Example 6

2-Pentafluoro-phenyl-imidazo[1,2-a]pyridine-6-carboxylic acid methyl ester

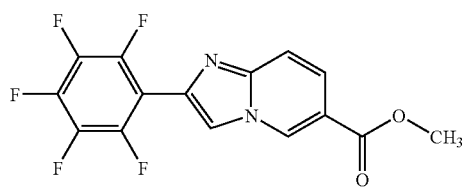 [SMILES: COC(=O)c1ccc2nc(-c3c(F)c(F)c(F)c(F)c3F)cn2c1]

The compound was synthesized analogously to example 1.
MS: M+H$^+$=343.06.

Example 7

2-p-Tolyl-imidazo[1,2-a]pyridine-6-carboxylic acid methyl ester

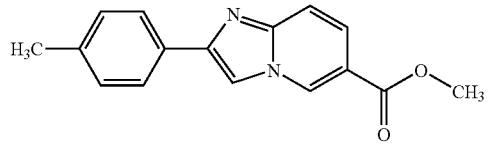

The compound was synthesized analogously to example 1.
MS: M+H$^+$=267.13.

Example 8

2-(3-Nitro-phenyl)-imidazo[1,2-a]pyridine-6-carboxylic acid methyl ester

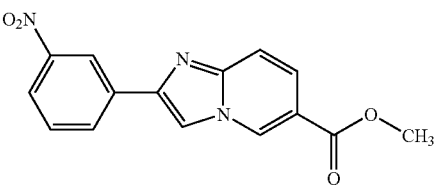 [SMILES: COC(=O)c1ccc2nc(-c3cccc([N+](=O)[O-])c3)cn2c1]

The compound was synthesized analogously to example 1.
MS: M+H$^+$=298.12.

Example 9

2-(4-Chloro-phenyl)-imidazo[1,2-a]pyridine-6-carboxylic acid methyl ester

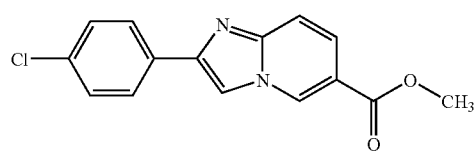 [SMILES: COC(=O)c1ccc2nc(-c3ccc(Cl)cc3)cn2c1]

The compound was synthesized analogously to example 1.
MS: M+H$^+$=287.08.

Example 10

2-(4-Methoxy-phenyl)-imidazo[1,2-a]pyridine-6-carboxylic acid methyl ester

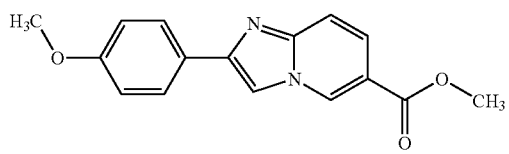

The compound was synthesized analogously to example 1.
MS: M+H$^+$=283.13.

Example 11

2-Naphthalen-2-yl-imidazo[1,2-a]pyridine-6-carboxylic acid methyl ester

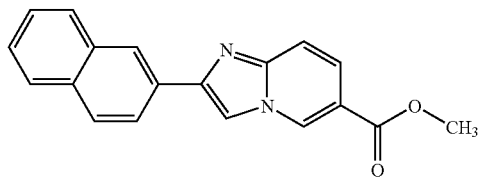 [SMILES: COC(=O)c1ccc2nc(-c3ccc4ccccc4c3)cn2c1]

The compound was synthesized analogously to example 1.
MS: M+H$^+$=303.13.

Example 12

2-(4-Bromo-phenyl)-imidazo[1,2-a]pyridine-6-carboxylic acid methyl ester

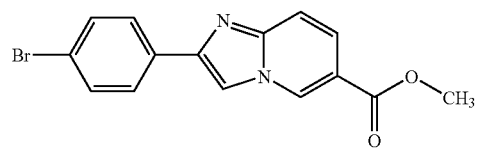

The compound was synthesized analogously to example 1.
MS: M+H$^+$=331.02.

Example 13

2-Phenyl-imidazo[1,2-a]pyridine-6-carboxylic acid methyl ester

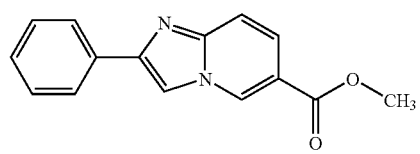 [SMILES: COC(=O)c1ccc2nc(-c3ccccc3)cn2c1]

The compound was synthesized analogously to example 1.
MS: M+H$^+$=253.11.

Example 14

2-(3-Fluoro-phenyl)-imidazo[1,2-a]pyridine-6-carboxylic acid methyl ester

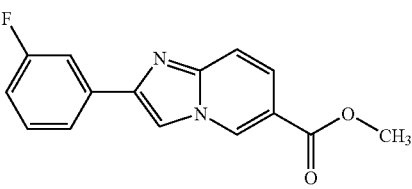 [SMILES: COC(=O)c1ccc2nc(-c3cccc(F)c3)cn2c1]

The compound was synthesized analogously to example 1.
MS: M+H$^+$=271.10.

Example 15

2-(4-Trifluoromethyl-phenyl)-imidazo[1,2-a]pyridine-6-carboxylic acid methyl ester

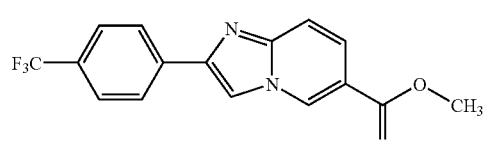

The compound was synthesized analogously to example 1.
MS: M+H$^+$=321.10.

Example 16

2-(4-Trifluoromethoxy-phenyl)-imidazo[1,2-a]pyridine-6-carboxylic acid methyl ester

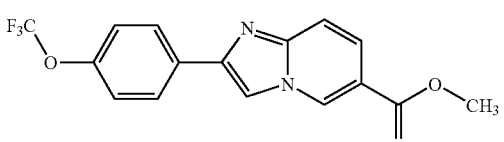

The compound was synthesized analogously to example 1.
MS: M+H$^+$=337.08.

Example 17

2-(4-Diethylamino-phenyl)-imidazo[1,2-a]pyridine-6-carboxylic acid methyl ester

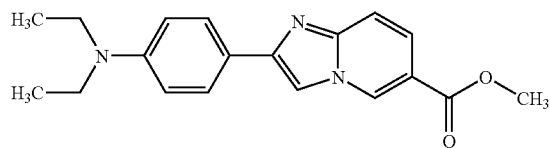 [SMILES: CCN(CC)c1ccc(-c2cn3cc(C(=O)OC)ccc3n2)cc1]

The compound was synthesized analogously to example 1. MS: M+H$^+$=324.18.

Example 18

2-(4-Cyano-phenyl)-imidazo[1,2-a]pyridine-6-carboxylic acid methyl ester

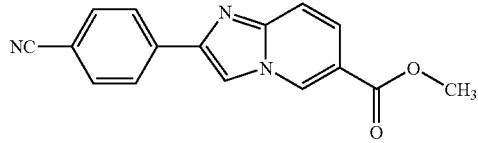

The compound was synthesized analogously to example 1. MS: M+H$^+$=278.12.

Example 19

2-(3,4-Difluoro-phenyl)-imidazo[1,2-a]pyridine-6-carboxylic acid methyl ester

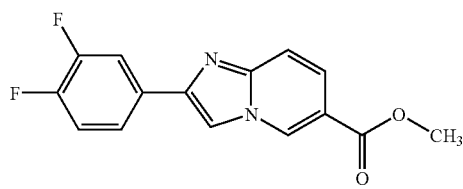 [SMILES: COC(=O)c1ccc2nc(-c3ccc(F)c(F)c3)cn2c1]

The compound was synthesized analogously to example 1. MS: M+H$^+$=289.07.

Example 20

2-(2-Chloro-phenyl)-imidazo[1,2-a]pyridine-6-carboxylic acid methyl ester

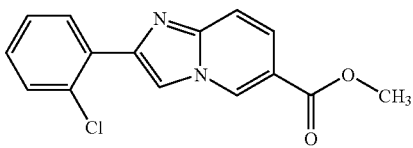

The compound was synthesized analogously to example 1. MS: M+H$^+$=287.05.

Example 21

2-(4-Bromo-3-sulfamoyl-phenyl)-imidazo[1,2-a]pyridine-6-carboxylic acid methyl ester

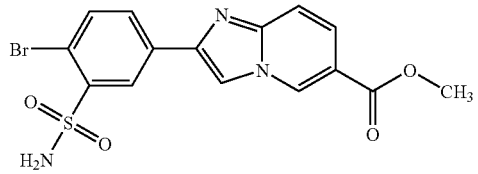 [SMILES: COC(=O)c1ccc2nc(-c3ccc(Br)c(S(N)(=O)=O)c3)cn2c1]

The compound was synthesized analogously to example 1. MS: M+H$^+$=410.03.

Example 22

2-(4-Fluoro-3-sulfamoyl-phenyl)-imidazo[1,2-a]pyridine-6-carboxylic acid methyl ester

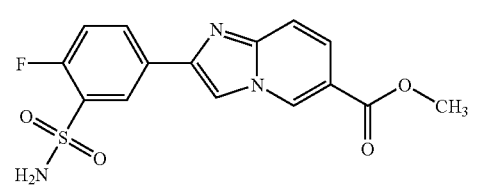 [SMILES: COC(=O)c1ccc2nc(-c3ccc(F)c(S(N)(=O)=O)c3)cn2c1]

The compound was synthesized analogously to example 1. MS: M+H$^+$=350.10.

Example 23

2-(3-Cyano-phenyl)-imidazo[1,2-a]pyridine-6-carboxylic acid methyl ester

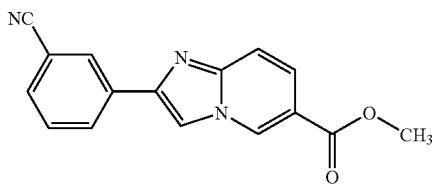

The compound was synthesized analogously to example 1. MS: M+H$^+$=278.12.

Example 24

2-(3-Bromo-phenyl)-imidazo[1,2-a]pyridine-6-carboxylic acid methyl ester

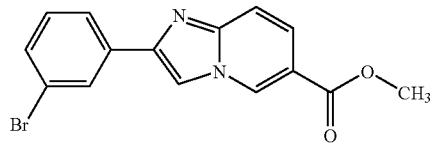 [SMILES: COC(=O)c1ccc2nc(-c3cccc(Br)c3)cn2c1]

The compound was synthesized analogously to example 1. MS: M+H$^+$=331.06.

Example 25

2-(2,4-Dimethyl-phenyl)-imidazo[1,2-a]pyridine-6-carboxylic acid methyl ester

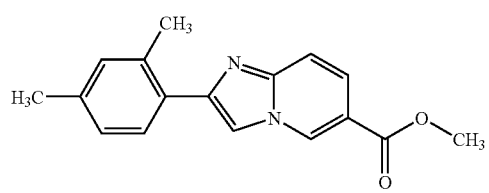

The compound was synthesized analogously to example 1. MS: M+H$^+$=281.15.

Example 26

2-(3,4-Dichloro-phenyl)-imidazo[1,2-a]pyridine-6-carboxylic acid methyl ester

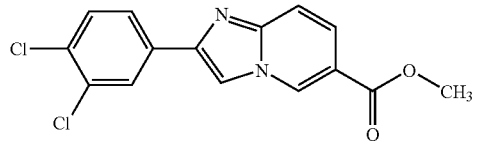 [SMILES: COC(=O)c1ccc2nc(-c3ccc(Cl)c(Cl)c3)cn2c1]

The compound was synthesized analogously to example 1. MS: M+H$^+$=321.04.

Example 27

2-(4-Chloro-3-methyl-phenyl)-imidazo[1,2-a]pyridine-6-carboxylic acid methyl ester

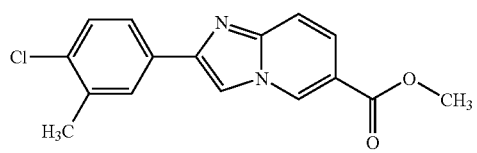 [SMILES: COC(=O)c1ccc2nc(-c3ccc(Cl)c(C)c3)cn2c1]

The compound was synthesized analogously to example 1. MS: M+H$^+$=301.09.

Example 28

2-(2,4-Dichloro-phenyl)-imidazo[1,2-a]pyridine-6-carboxylic acid methyl ester

The compound was synthesized analogously to example 1. MS: M+H$^+$=321.07.

Example 29

2-(4-Cyclohexyl-phenyl)-imidazo[1,2-a]pyridine-6-carboxylic acid methyl ester

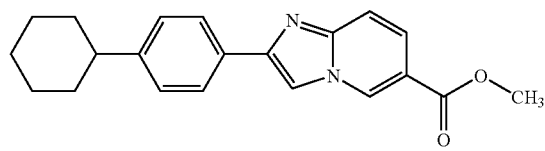 [SMILES: COC(=O)c1ccc2nc(-c3ccc(C4CCCCC4)cc3)cn2c1]

The compound was synthesized analogously to example 1. MS: M+H$^+$=335.20.

Example 30

2-(4-Methanesulfonyl-phenyl)-imidazo[1,2-a]pyridine-6-carboxylic acid methyl ester

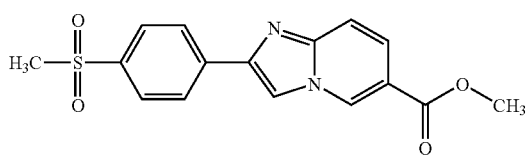

The compound was synthesized analogously to example 1. MS: M+H$^+$=331.09.

Example 31

2-(3-Chloro-phenyl)-imidazo[1,2-a]pyridine-6-carboxylic acid methyl ester

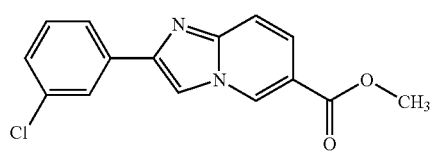 [SMILES: COC(=O)c1ccc2nc(-c3cccc(Cl)c3)cn2c1]

The compound was synthesized analogously to example 1. MS: M+H$^+$=287.08.

Example 32

2-(3,5-Difluoro-phenyl)-imidazo[1,2-a]pyridine-6-carboxylic acid methyl ester

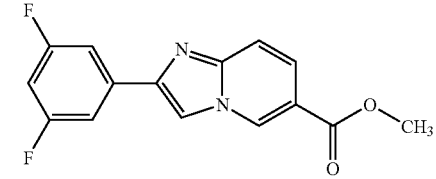 [SMILES: COC(=O)c1ccc2nc(-c3cc(F)cc(F)c3)cn2c1]

The compound was synthesized analogously to example 1. MS: M+H$^+$=289.07.

Example 33

2-(3-Trifluoromethyl-phenyl)-imidazo[1,2-a]pyridine-6-carboxylic acid methyl ester

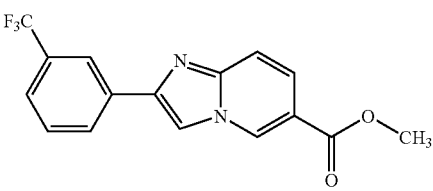 [SMILES: COC(=O)c1ccc2nc(-c3cccc(C(F)(F)F)c3)cn2c1]

The compound was synthesized analogously to example 1. MS: M+H$^+$=321.07.

Example 34

2-(2,3-Dihydro-benzo[1,4]dioxin-6-yl)-imidazo[1,2-a]pyridine-6-carboxylic acid methyl ester

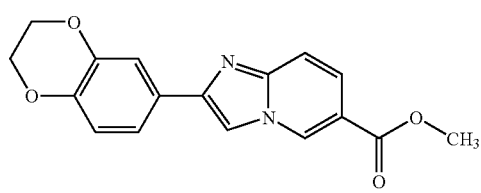 [SMILES: COC(=O)c1ccc2nc(-c3ccc4c(c3)OCCO4)cn2c1]

The compound was synthesized analogously to example 1. MS: M+H$^+$=311.09.

Example 35

2-(2,6-Dichloro-4-trifluoromethyl-phenyl)-imidazo[1,2-a]pyridine-6-carboxylic acid methyl ester

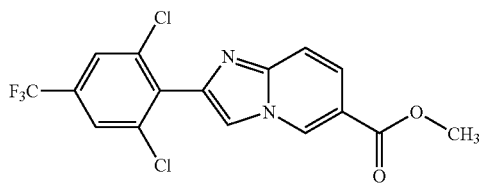 [SMILES: COC(=O)c1ccc2nc(-c3c(Cl)cc(C(F)(F)F)cc3Cl)cn2c1]

The compound was synthesized analogously to example 1. MS: M+H$^+$=389.10.

Example 36

2-(2-Nitro-phenyl)-imidazo[1,2-a]pyridine-6-carboxylic acid methyl ester

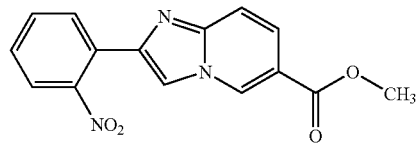 [SMILES: COC(=O)c1ccc2nc(-c3ccccc3[N+](=O)[O-])cn2c1]

The compound was synthesized analogously to example 1. MS: M+H$^+$=289.09.

Example 37

2-Biphenyl-4-yl-imidazo[1,2-a]pyridine-6-carboxylic acid methyl ester

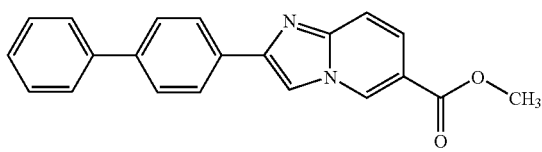 [SMILES: COC(=O)c1ccc2nc(-c3ccc(-c4ccccc4)cc3)cn2c1]

The compound was synthesized analogously to example 1. MS: M+H$^+$=329.16.

Example 38

2-(4-Nitro-phenyl)-imidazo[1,2-a]pyridine-6-carboxylic acid methyl ester

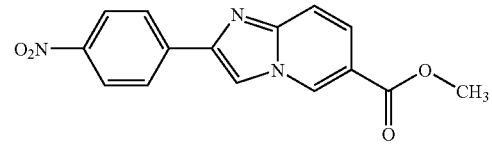

The compound was synthesized analogously to example 1. Yield: 91%. MS: M+H$^+$=298.04.

Example 39

2-(4-Sulfamoyl-phenyl)-imidazo[1,2-a]pyridine-6-carboxylic acid methyl ester

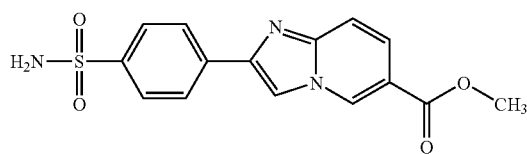 [SMILES: COC(=O)c1ccc2nc(-c3ccc(S(N)(=O)=O)cc3)cn2c1]

The compound was synthesized analogously to example 1. MS: M+H$^+$=232.02.

Example 40

2-(4-Sulfamoyl-phenyl)-imidazo[1,2-a]pyridine-6-carboxylic acid methyl ester

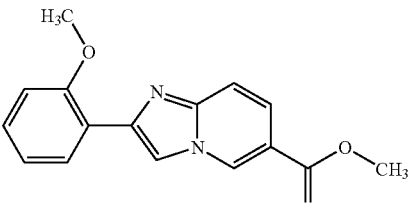

The compound was synthesized analogously to example 1. MS: M+H$^+$=283.19.

Example 41

2-(2-Trifluoromethyl-phenyl)-imidazo[1,2-a]pyridine-6-carboxylic acid methyl ester

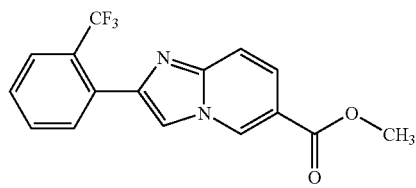 [SMILES: COC(=O)c1ccc2nc(-c3ccccc3C(F)(F)F)cn2c1]

The compound was synthesized analogously to example 1. MS: M+H$^+$=321.10.

Example 42

11H-Indeno[1',2':4,5]imidazo[1,2-a]pyridine-8-carboxylic acid methyl ester

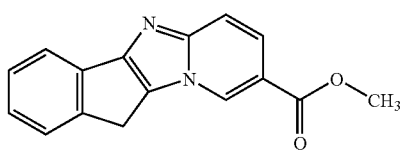 [SMILES: COC(=O)c1ccc2nc3c(n2c1)Cc1ccccc1-3]

The compound was synthesized analogously to example 1. MS: M+H$^+$=265.05.

Example 43

2-(4-Pyrrolidin-1-yl-phenyl)-imidazo[1,2-a]pyridine-6-carboxylic acid methyl ester

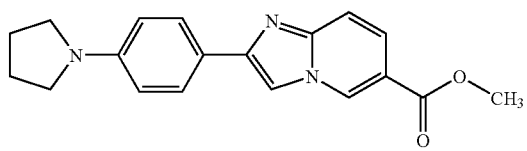 [SMILES: COC(=O)c1ccc2nc(-c3ccc(N4CCCC4)cc3)cn2c1]

The compound was synthesized analogously to example 1. MS: M+H$^+$=322.15.

Example 44

2-(4-Amino-phenyl)-imidazo[1,2-a]pyridine-6-carboxylic acid methyl ester

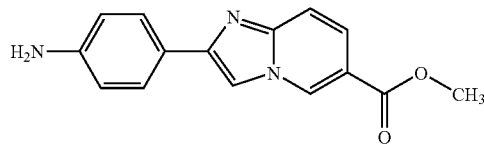

The compound was synthesized by hydrogenation of 2-(4-Nitro-phenyl)-imidazo[1,2-a]pyridine-6-carboxylic acid methyl ester (example 38). Yield: 83%. MS: M+H$^+$=268.09.

Example 45

2-(4-Fluoro-phenyl)-imidazo[1,2-a]pyridine-6-carboxylic acid

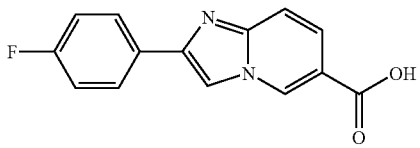 [SMILES: O=C(O)c1ccc2nc(-c3ccc(F)cc3)cn2c1]

2-(4-Fluoro-phenyl)-imidazo[1,2-a]pyridine-6-carboxylic acid methyl ester (example 1; 590 mg, 2.18 mmol) was heated in 5 ml hydrobromic acid (48%) and 15 ml acetic acid at 120° C. for 10 hours. The solid was filtered, washed and dried. Yield: 38%. MS: M+H$^+$=257.04.

Example 46

2-p-Tolyl-imidazo[1,2-a]pyridine-6-carboxylic acid

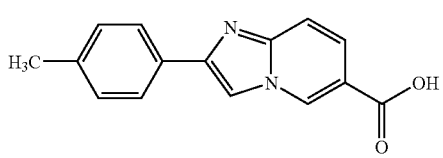 [SMILES: Cc1ccc(-c2cn3cc(C(=O)O)ccc3n2)cc1]

The compound was synthesized analogously to example 45 using example 7. Yield: 26%. MS: M+H$^+$=253.04.

Example 47

2-(4-Diethylamino-phenyl)-imidazo[1,2-a]pyridine-6-carboxylic acid hydrobromide

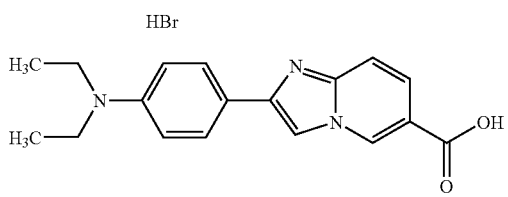 [SMILES: Br ; CCN(CC)c1ccc(-c2cn3cc(C(=O)O)ccc3n2)cc1]

The compound was synthesized analogously to example 45 using example 17. Yield: 17%. MS: M+H$^+$=310.08.

Example 48

2-(4-Fluoro-phenyl)-imidazo[1,2-a]pyridine-6-carboxylic acid tert-butylamide

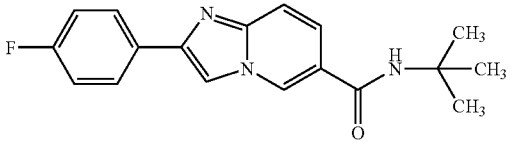 [SMILES: CC(C)(C)NC(=O)c1ccc2nc(-c3ccc(F)cc3)cn2c1]

2-(4-Fluoro-phenyl)-imidazo[1,2-a]pyridine-6-carboxylic acid (example 45; 40 mg, 0.14 mmol), tert-butylamine (73.1 mg, 0.0.27 mmol), HATU (O-(7-azabenzotriazol-1-yl)-N,N,N',N'-tetramethyluronium hexafluorophosphate; 57.2 mg, 0.15 mmol) and triethylamine (56.8 µl, 0.41 mmol) in 3 ml DMF were stirred at room temperature for 2 hours. The mixture was evaporated. ethyl acetate and water were added, the organic layer was separated, washed with water, dried and evaporated. The crude product was purified by preparative HPLC (RP18, acetonitrile/water 0.1% TFA) to yield 44 mg (99%) of the desired product. MS: M+H$^+$=312.15.

Example 49

2-(4-Fluoro-phenyl)-imidazo[1,2-a]pyridine-6-carboxylic acid amide

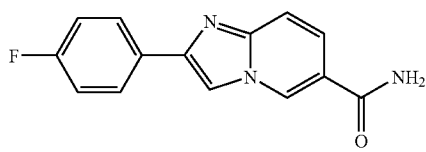 [SMILES: NC(=O)c1ccc2nc(-c3ccc(F)cc3)cn2c1]

The compound was synthesized analogously to example 48. Yield: 47%. MS: M+H$^+$=256.09.

Example 50

2-(4-Fluoro-phenyl)-imidazo[1,2-a]pyridine-6-carboxylic acid dimethylamide

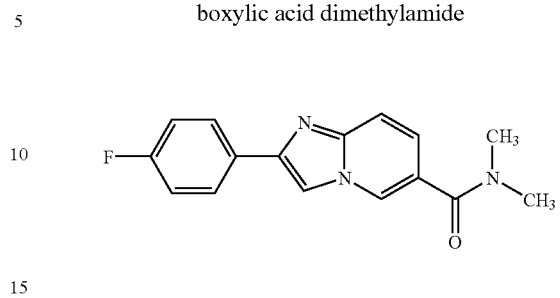

The compound was synthesized analogously to example 48. Yield: 12%. MS: M+H$^+$=284.21.

Example 51

Azetidin-1-yl-[2-(4-fluoro-phenyl)-imidazo[1,2-a]pyridin-6-yl]-methanone

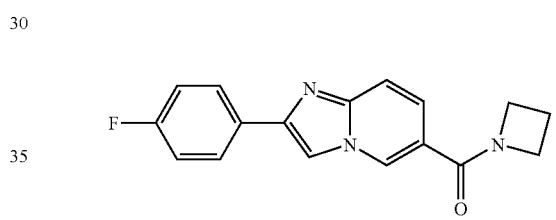

The compound was synthesized analogously to example 48. Yield: 25%. MS: M+H$^+$=296.13.

Example 52

2-(4-Fluoro-phenyl)-imidazo[1,2-a]pyridine-6-carbonitrile

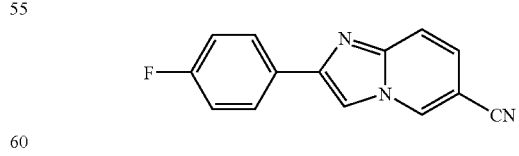

2-Bromo-1-(4-fluoro-phenyl)-ethanone (2.08 g, 9.6 mmol) and 6-amino-nicotinonitrile (1.14 g, 9.6 mmol) were heated under reflux in 50 ml dioxane for 13 hours. After cooling the solid was filtered and purified by preparative HPLC (RP18, acetonitrile/water 0.1% TFA) to yield 1.05 g (46%) of the desired product. MS: M+H$^+$=238.04.

Example 53

2-(4-Diethylamino-phenyl)-imidazo[1,2-a]pyridine-6-carbonitrile trifluoroacetic acid salt

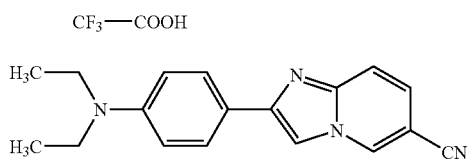

The compound was synthesized analogously to example 52. Yield: 29%. MS: M+H⁺=291.17.

Example 54

2-p-Tolyl-imidazo[1,2-a]pyridine-6-carbonitrile

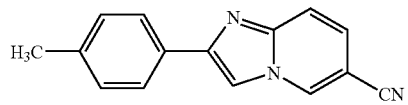

The compound was synthesized analogously to example 52. Yield: 31%. MS: M+H⁺=234.04.

Example 55

2-(3-Chloro-phenyl)-imidazo[1,2-a]pyridine-6-carbonitrile

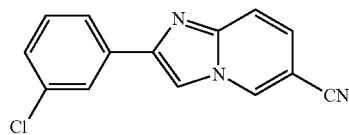 [SMILES: N#Cc1ccc2nc(-c3cccc(Cl)c3)cn2c1]

The compound was synthesized analogously to example 52. Yield: 62%. MS: M+H⁺=254.05.

Example 56

2-(4-Fluoro-phenyl)-N-hydroxy-imidazo[1,2-a]pyridine-6-carboxamidine

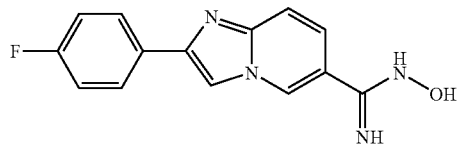 [SMILES: N=C(NO)c1ccc2nc(-c3ccc(F)cc3)cn2c1]

2-(4-Fluoro-phenyl)-imidazo[1,2-a]pyridine-6-carbonitrile (example 52, 537 mg, 2.26 mmol), hydroxylamine hydrochloride (943.8 mg, 13.58 mmol) and triethylamine (2.19 ml, 15.84 mmol) were stirred in 40 ml of isopropanol at 90° C. for 5 hours. The solvent was removed in vacuo and water was added. The solid was filtered, washed with diluted hydrochloric acid, water and was dried. Yield: 610 mg, 99%. MS: M+H⁺=271.03.

Example 57

N-Hydroxy-2-p-tolyl-imidazo[1,2-a]pyridine-6-carboxamidine

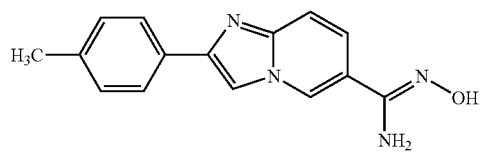

The compound was synthesized analogously to example 57 using example 54. Yield: 62%. MS: M+H⁺=267.08.

Example 58

2-(4-Diethylamino-phenyl)-N-hydroxy-imidazo[1,2-a]pyridine-6-carboxamidine trifluoroacetic acid salt

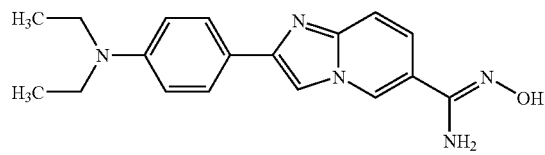

The compound was synthesized analogously to example 56 using example 53. Yield: 50%. MS: M+H⁺=324.10.

Example 59

2-(3-Chloro-phenyl)-N-hydroxy-imidazo[1,2-a]pyridine-6-carboxamidine

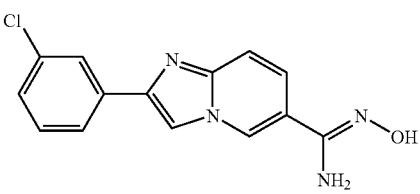 [SMILES: N/C(=N\O)c1ccc2nc(-c3cccc(Cl)c3)cn2c1]

The compound was synthesized analogously to example 56 using example 55. Yield: 59%. MS: M+H⁺=287.00.

Example 60

2-(4-Fluoro-phenyl)-N-ethoxycarbonyloxy-imidazo[1,2-a]pyridine-6-carboxamidine

2-(4-Fluoro-phenyl)-N-hydroxy-imidazo[1,2-a]pyridine-6-carboxamidine (example 56; 85.1 mg, 0.315 mmol) was dissolved in 5 ml DMF. The mixture was heated to 80° C. after addition of triethylamine (87.8 µl, 0.63 mmol) and ethyl chloroformate (33 µl, 0.34 mmol) for 2.5 hours. The mixture was evaporated. Ethyl acetate and water were added, the organic layer was separated, washed with water, dried and evaporated. The crude product was purified by preparative HPLC (RP18, acetonitrile/water 0.1% TFA) to yield 48 mg (45%) of the desired product. MS: M+H$^+$=343.05.

Example 61

6-Bromo-2-(4-fluoro-phenyl)-imidazo[1,2-a]pyridine

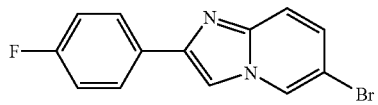

The compound was synthesized analogously to example 52. Yield: 51%. MS: M+H$^+$=290.99.

Example 62

6-Bromo-2-p-tolyl-imidazo[1,2-a]pyridine

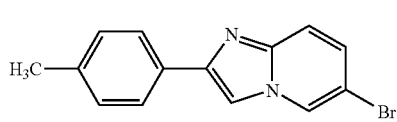 [SMILES: Cc1ccc(-c2cn3cc(Br)ccc3n2)cc1]

The compound was synthesized analogously to example 52. Yield: 48%. MS: M+H$^+$=287.00.

Example 63

6-Bromo-2-(3-chloro-phenyl)-imidazo[1,2-a]pyridine

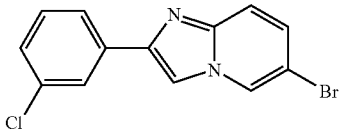 [SMILES: Clc1cccc(-c2cn3cc(Br)ccc3n2)c1]

The compound was synthesized analogously to example 52. Yield: 41%. MS: M+H$^+$=306.99.

Example 64

[4-(6-Bromo-imidazo[1,2-a]pyridin-2-yl)-phenyl]-diethyl-amine trifluoroacetic acid salt

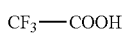
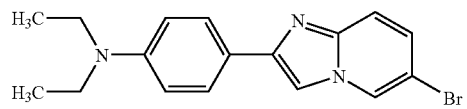

The compound was synthesized analogously to example 52. Yield: 39%. MS: M+H$^+$=344.01.

Example 65

2-(4-Fluoro-phenyl)-6-nitro-imidazo[1,2-a]pyridine

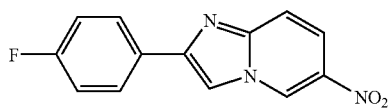

The compound was synthesized analogously to example 52. Yield: 20%. MS: M+H$^+$=258.08.

Example 66

2-(4-Fluoro-phenyl)-imidazo[1,2-a]pyridin-6-ylamine

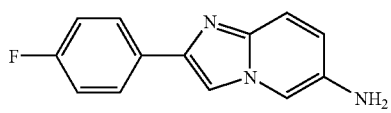

The compound was synthesized by hydrogenation of 2-(4-fluoro-phenyl)-6-nitro-imidazo[1,2-a]pyridine (example 65). Yield: 20%. MS: M+H$^+$=228.08.

Example 67

N-[2-(4-Fluoro-phenyl)-imidazo[1,2-a]pyridin-6-yl]-formamide

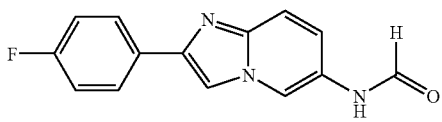

The compound was synthesized by formylation of 2-(4-fluoro-phenyl)-imidazo[1,2-a]pyridin-6-ylamine (example 66). Yield: 48%. MS: M+H$^+$=256.08.

Example 68

N-[2-(4-Fluoro-phenyl)-imidazo[1,2-a]pyridin-6-yl]-acetamide

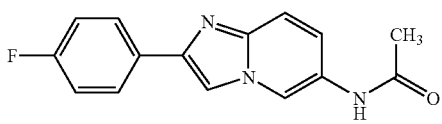 [SMILES: CC(=O)Nc1ccc2nc(-c3ccc(F)cc3)cn2c1]

The compound was synthesized by acetylation of 2-(4-fluoro-phenyl)-imidazo[1,2-a]pyridin-6-ylamine (example 66). Yield: 37%. MS: M+H$^+$=270.10.

Example 69

3-[2-(4-Fluoro-phenyl)-imidazo[1,2-a]pyridin-6-yl]-imidazolidine-2,4-dione

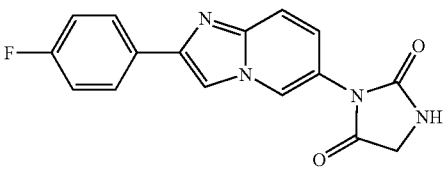 [SMILES: O=C1CNC(=O)N1c1ccc2nc(-c3ccc(F)cc3)cn2c1]

The compound was synthesized analogously to example 52. Yield: 57%. MS: M+H$^+$=311.12.

Example 70

3-[2-(4-Fluoro-phenyl)-imidazo[1,2-a]pyridin-6-yl]-4H-1,2,4-oxadiazol-5-one

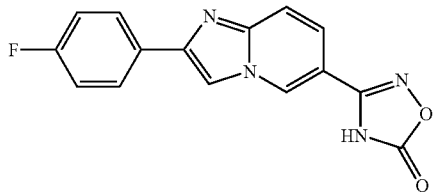 [SMILES: O=c1[nH]c(-c2ccc3nc(-c4ccc(F)cc4)cn3c2)no1]

The compound was synthesized by treatment of 2-(4-fluoro-phenyl)-N-ethoxycarbonyloxy-imidazo[1,2-a]pyridine-6-carboxamidine (example 60) with aqueous sodium carbonate. Yield: 14%. MS: M+H$^+$=296.95.

Example 71

2-(4-Fluoro-phenyl)-imidazo[1,2-a]pyridine-6-carboxamidine trifluoroacetic acid salt

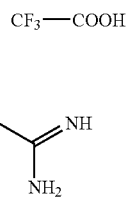

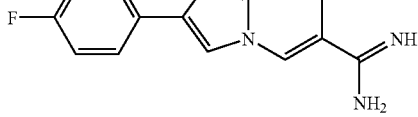

The compound was synthesized by treatment of 2-(4-fluoro-phenyl)-imidazo[1,2-a]pyridine-6-carbonitrile (example 52) with hydrochloric acid in ethanol and subsequent reaction with ammonia. Yield: 75%. MS: M+H$^+$=255.09.

Determination of the Biological Activity

A) Activation of eNOS Transcription

Activation of eNOS transcription was measured as described in detail by Li et al., "Activation of protein kinase C alpha and/or epsilon enhances transcription of the human endothelial nitric oxide synthase gene", Mol. Pharmacol. 53 (1998) 630. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with the compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No. E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. EC$_{50}$ values of transcription induction ratios as a function of compound concentration were determined graphically.

Numerous compounds of the instant invention were tested by the above-described assay and found to increase protein transcription. Generally, the tested compounds exhibited $EC_{50}$ values of less than about 50 µM. Preferred compounds exhibited $EC_{50}$ values of from about 5 µM to about 0.5 µM. More preferred compounds, for example the compounds of examples 1, 2, 3, 5, 7, 8, 10, 12, 13, 14, 15, 16, 17, 19, 20, 21, 23, 24, 25, 28, 31, 32, 33, 34, 37, 38, 42, 44, 46, 52, 53, 54, 56, 57, 60, 61, 66 and 67 exhibited $EC_{50}$ values of less than 0.5 µM.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compound incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemofluorescence detection method.

The effect of the compounds of the formulae I, Ia and Ib can also be investigated in the following animal models (animal experiments are performed in accordance with the German animal protection law and the guidelines for the use of experimental animals as given by the Guide for the Care and Use of Laboratory Animals of the US National Institutes of Health).
Animals and Treatment (Experiments B-E)

ApoE and eNOS deficient mice (C57BL/6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% of fat and 0.001% of cholesterol; in the following designated as placebo group) or a standard rodent chow+test compound (10 or 30 mg/kg/day p.o.).
B) Anti-Hypertensive Effect in ApoE Knockout Mice Blood-pressure is determined in conscious mice using a computerized tail-cuff system (Visitech Systems, Apex, N.C.). After treatment of ApoE deficient mice and eNOS deficient mice with the test compounds the blood pressure is compared to the results obtained with a placebo treatment.
C) Inhibition of Neointima Formation and Atherogenesis (Femoral Artery Cuff)

After 3 day treatment of ApoE deficient mice with the respective compound (10 mg/kg/day pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al. (J. Clin. Invest. 101 (1998) 1225). Briefly, the left femoral artery is dissected. A non-occlusive 2.0 mm polyethylene cuff made of PE 50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 µm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.
D) Prevention of Atherosclerotic Plaque Formation in Chronic Treatment ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.
E) Improvement of Coronary Function in Diseased ApoE Deficient Mice Old Male wild-type C57BL/6J mice (Charles River Wiga GmbH, Sulzfeld), and apoE deficient mice (C57BL/6J background, Jackson Laboratory, Bar Harbor, Me.) of 6 month of age and weighing 28 to 36 g are used in the experiments. Mice are divided into 3 groups (C57BL/6J, n=8; apoE control, n=8; apoE with respective compound, n=8) and receive for 8 weeks either a standard rodent chow (containing 4% of fat and 0.001% of cholesterol) or a standard rodent chow+respective compound (30 mg/kg/day p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using specialized software (HEM, Notocord).

Hearts are allowed to stabilize for 30 min. All functional hemodynamic data are measured during steady state, and during volume and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure and volume loading.

We claim:

1. A pharmaceutical composition comprising at least one compound of formula Ia,

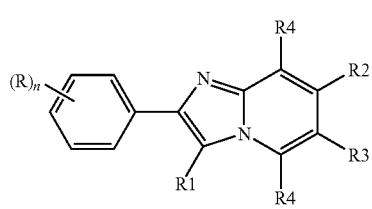

or a physiologically acceptable salt thereof, and a pharmaceutically acceptable carrier, in which R is chosen from halogen, $(C_1\text{-}C_6)$-alkyl which can be substituted by one or more fluorine atoms, $(C_1\text{-}C_3)$-alkoxy-$(C_1\text{-}C_3)$-alkyl, hydroxy, $(C_1\text{-}C_6)$-alkoxy which can be substituted by one or more fluorine atoms, $(C_1\text{-}C_6)$-alkylmercapto, NR7R8, mono-$(C_1\text{-}C_6)$-alkylaminocarbonyl, di-$(C_2\text{-}C_6)$-alkylamino carbonyl, $(C_1\text{-}C_6)$- alkoxycarbonyl, cyano, $(C_1\text{-}C_6)$-alkylsulfinyl, $(C_1\text{-}C_6)$-alkylsulfonyl, aminosulfonyl, nitro, pentafluorosulfanyl, $(C_3\text{-}C_7)$-cycloalkyl and $(C_6\text{-}C_{14})$-aryl, wherein the aryl residue can be substituted by one or more identical or different substituents chosen from halogen, $(C_1\text{-}C_6)$-alkyl, $(C_1\text{-}C_6)$-alkoxy and trifluoromethyl;

or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;

R1 is chosen from hydrogen and $(C_1\text{-}C_6)$-alkyl;

or R and R1 form together a $(C_1\text{-}C_2)$-alkylene or $(C_1\text{-}C_2)$-alkenylene chain if R is attached in ortho-position of the phenyl ring;

R2 is chosen from hydrogen, hydroxy and $(C_1\text{-}C_6)$-alkyl;

R3 is chosen from Br, cyano, nitro, —C(=O)—NR9R10, amino, —N(R11)-C(=O)—R12, COOH, $(C_1\text{-}C_6)$-alkoxycarbonyl and —C(=NR5)-NHR6;

R4 is each time independently chosen from hydrogen and $(C_1\text{-}C_6)$-alkyl;

R5 is chosen from hydrogen, $(C_1\text{-}C_6)$-alkyl, $(C_1\text{-}C_6)$-alkylcarbonyl, $(C_1\text{-}C_6)$-alkoxycarbonyl, $(C_1\text{-}C_6)$-alkoxycarbonyloxy, $(C_1\text{-}C_{18})$-alkylcarbonyloxy-$(C_1\text{-}C_6)$-alkoxycarbonyl, $(C_6\text{-}C_{14})$-arylcarbonyl, $(C_6\text{-}C_{14})$-aryloxycarbonyl, hydroxy, $(C_1\text{-}C_6)$-alkylcarbonyloxy, $(C_6\text{-}C_{14})$-aryl-$(C_1\text{-}C_6)$-alkoxycarbonyl, $(C_1\text{-}C_6)$-alkylaminocarbonyloxy, di-$((C_1\text{-}C_6)$-alkyl)aminocarbonyloxy, $(C_1\text{-}C_6)$-alkylaminocarbonyl and di-$((C_1\text{-}C_6)$-alkyl)aminocarbonyl, wherein all aryl groups can be substituted by one or more identical or different substituents chosen from halogen, $(C_1\text{-}C_6)$-alkyl, $(C_1\text{-}C_6)$-alkoxy and trifluoromethyl;

R6 is chosen from hydrogen, cyano, hydroxy, $(C_1\text{-}C_6)$-alkoxy and $(C_6\text{-}C_{14})$-aryl-$(C_1\text{-}C_6)$ alkoxy;

or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;

R7 and R8 are independently chosen from hydrogen and $(C_1\text{-}C_6)$-alkyl;

or R7 and R8 form, together with the nitrogen atom which carries them, a 4-membered to 7-membered, saturated, partially unsaturated or aromatic heterocyclic ring;

R9 and R10 are independently chosen from hydrogen and $(C_1\text{-}C_6)$-alkyl;

or R9 and R10 form, together with the nitrogen atom which carries them, a 4-membered to 7-membered, saturated, partially unsaturated or aromatic heterocyclic ring;

R11 is chosen from hydrogen and $(C_1\text{-}C_6)$-alkyl;

R12 is chosen from hydrogen and $(C_1\text{-}C_6)$-alkyl;

or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;

R13, R14 and R15 are independently chosen from halogen, $(C_1\text{-}C_6)$-alkyl, $(C_1\text{-}C_6)$-alkoxy and trifluoromethyl;

n is chosen from 0, 1, 2, 3, 4 and 5;

provided that compounds are excluded in which R1, R2 and R4 are hydrogen, n is 1, R is cyano and R3 is cyano, $(C_1\text{-}C_6)$-alkoxycarbonyl or COOH, provided that compounds are excluded in which R1 is hydrogen or methyl, R2 and R4 are hydrogen, n is 1, R3 is COOH or $(C_1\text{-}C_6)$-alkoxycarbonyl, and R is Cl, provided that compounds are excluded in which R1, R2 and R4 are hydrogen and n is 0, and provided that compounds are excluded in which R1, R2 and R4 are hydrogen, R3 is Br, n is 1, and R is Br, NO$_2$, dimethylamino, amino, methyl, amide or F.

2. The pharmaceutical composition as claimed in claim 1, wherein in the compound of formula Ia R is chosen from halogen, $(C_1\text{-}C_6)$-alkyl which can be substituted by one or more fluorine atoms, $(C_1\text{-}C_6)$-alkoxy which can be substituted by one or more fluorine atoms, NR7R8, cyano, $(C_1\text{-}C_6)$-alkylsulfonyl, aminosulfonyl, nitro, $(C_3\text{-}C_7)$-cycloalkyl and $(C_6\text{-}C_{14})$-aryl;

or two adjacent R groups form, together with the carbon atoms which carry them, a 4-membered to 7-membered, partially unsaturated or aromatic heterocyclic ring and which can contain one or two ring members chosen from —N(R4)-, —C(=O)— and —O— which can be identical or different;

R1 is chosen from hydrogen and $(C_1\text{-}C_6)$-alkyl;

or R and R1 form together a (C1-C2)-alkylene chain if R is attached in ortho-position of the phenyl ring;

R2 is hydrogen;

R3 is chosen from Br, cyano, nitro, —C(=O)—NR9R10, amino, —N(R11)-C(=O)—R12, COOH, $(C_1-C_6)$-alkoxycarbonyl and —C(=NR5)-NHR6;

R4 is each time hydrogen;

R5 is chosen from hydrogen, $(C_1-C_6)$-alkoxycarbonyloxy and hydroxy;

R6 is hydrogen;

or R5 and R6 form, together with the —N=C—NH— group which carries them, a 4-membered to 7-membered, partially unsaturated or aromatic heterocyclic ring and which, in addition to the nitrogen atoms being part of the —N=C—NH— group, can contain one or two further ring members chosen from —C(=O)— and —O—;

R7 and R8 are independently chosen from hydrogen, $(C_1-C_6)$-alkyl;

or R7 and R8 form, together with the nitrogen atom which carries them, a 4-membered to 7-membered, saturated, partially unsaturated or aromatic heterocyclic ring;

R9 and R10 are independently chosen from hydrogen and $(C_1-C_6)$-alkyl;

or R9 and R10 form, together with the nitrogen atom which carries them, a 4-membered to 7-membered, saturated, partially unsaturated or aromatic heterocyclic ring;

R11 is hydrogen;

R12 is chosen from hydrogen and $(C_1-C_6)$-alkyl;

or R11 and R12 form, together with the carbonylamino group which carries them, a 4-membered to 7-membered, saturated, partially unsaturated or aromatic heterocyclic ring and which, in addition to the carbonylamino group connecting R11 and R12, can contain one or two further ring members chosen from —N(R4)- and —C(=O)—; and n is chosen from 0, 1, 2, 3, 4 and 5;

provided that compounds are excluded in which R1, R2 and R4 are hydrogen, n is 1, R is cyano and R3 is cyano, $(C_1-C_6)$-alkoxycarbonyl or COOH, provided that compounds are excluded in which R1 is hydrogen or methyl, R2 and R4 are hydrogen, n is 1, R3 is COOH or $(C_1-C_6)$-alkoxycarbonyl, and R is Cl, provided that compounds are excluded in which R1, R2 and R4 are hydrogen and n is 0, and provided that compounds are excluded in which R1, R2 and R4 are hydrogen, R3 is Br, n is 1, and R is Br, NO$_2$, dimethylamino, amino, methyl, amide or F.

3. The pharmaceutical composition as claimed in claim 1, wherein the compound of formula Ia is chosen from:

2-(4-fluoro-phenyl)-imidazo[1,2-a]pyridine-6-carboxylic acid methyl ester, 2-(4-bromo-phenyl)-3-methyl-imidazo[1,2-a]pyridine-6-carboxylic acid methyl ester, 3-methyl-2-phenyl-imidazo[1,2-a]pyridine-6-carboxylic acid methyl ester, 2-(2-oxo-1,2,3,4-tetrahydro-quinolin-6-yl)-imidazo[1,2-a]pyridine-6-carboxylic acid methyl ester, 2-(2-fluoro-phenyl)-imidazo[1,2-a]pyridine-6-carboxylic acid methyl ester, 2-pentafluoro-phenyl-imidazo[1,2-a]pyridine-6-carboxylic acid methyl ester, 2-p-tolyl-imidazo[1,2-a]pyridine-6-carboxylic acid methyl ester, 2-(3-nitro-phenyl)-imidazo[1,2-a]pyridine-6-carboxylic acid methyl ester, 2-(4-methoxy-phenyl)-imidazo[1,2-a]pyridine-6-carboxylic acid methyl ester, 2-naphthalen-2-yl-imidazo[1,2-a]pyridine-6-carboxylic acid methyl ester, 2-(4-bromo-phenyl)-imidazo[1,2-a]pyridine-6-carboxylic acid methyl ester, 2-(3-fluoro-phenyl)-imidazo[1,2-a]pyridine-6-carboxylic acid methyl ester, 2-(4-trifluoromethyl-phenyl)-imidazo[1,2-a]pyridine-6-carboxylic acid methyl ester, 2-(4-trifluoromethoxy-phenyl)-imidazo[1,2-a]pyridine-6-carboxylic acid methyl ester, 2-(4-diethylamino-phenyl)-imidazo[1,2-a]pyridine-6-carboxylic acid methyl ester, 2-(4-cyano-phenyl)-imidazo[1,2-a]pyridine-6-carboxylic acid methyl ester, 2-(2-chloro-phenyl)-imidazo[1,2-a]pyridine-6-carboxylic acid methyl ester, 2-(4-bromo-3-sulfamoyl-phenyl)-imidazo[1,2-a]pyridine-6-carboxylic acid methyl ester, 2-(4-fluoro-3-sulfamoyl-phenyl)-imidazo[1,2-a]pyridine-6-carboxylic acid methyl ester, 2-(3-cyano-phenyl)-imidazo[1,2-a]pyridine-6-carboxylic acid methyl ester, 2-(3-bromo-phenyl)-imidazo[1,2-a]pyridine-6-carboxylic acid methyl ester, 2-(2,4-dimethyl-phenyl)-imidazo[1,2-a]pyridine-6-carboxylic acid methyl ester, 2-(3,4-dichloro-phenyl)-imidazo[1,2-a]pyridine-6-carboxylic acid methyl ester, 2-(4-chloro-3-methyl-phenyl)-imidazo[1,2-a]pyridine-6-carboxylic acid methyl ester, 2-(2,4-dichloro-phenyl)-imidazo[1,2-a]pyridine-6-carboxylic acid methyl ester, 2-(4-cyclohexyl-phenyl)-imidazo[1,2-a]pyridine-6-carboxylic acid methyl ester, 2-(4-methanesulfonyl-phenyl)-imidazo[1,2-a]pyridine-6-carboxylic acid methyl ester, 2-(3-chloro-phenyl)-imidazo[1,2-a]pyridine-6-carboxylic acid methyl ester, 2-(3,5-difluoro-phenyl)-imidazo[1,2-a]pyridine-6-carboxylic acid methyl ester, 2-(3-trifluoromethyl-phenyl)-imidazo[1,2-a]pyridine-6-carboxylic acid methyl ester, 2-(2,3-dihydro-benzo[1,4]dioxin-6-yl)-imidazo[1,2-a]pyridine-6-carboxylic acid methyl ester, 2-(2,6-dichloro-4-trifluoromethyl-phenyl)-imidazo[1,2-a]pyridine-6-carboxylic acid methyl ester, 2-(2-nitro-phenyl)-imidazo[1,2-a]pyridine-6-carboxylic acid methyl ester, 2-biphenyl-4-yl-imidazo[1,2-a]pyridine-6-carboxylic acid methyl ester, 2-(4-nitro-phenyl)-imidazo[1,2-a]pyridine-6-carboxylic acid methyl ester, 2-(4-sulfamoyl-phenyl)-imidazo[1,2-a]pyridine-6-carboxylic acid methyl ester, 2-(4-sulfamoyl-phenyl)-imidazo[1,2-a]pyridine-6-carboxylic acid methyl ester, 2-(2-trifluoromethyl-phenyl)-imidazo[1,2-a]pyridine-6-carboxylic acid methyl ester, 11H-indeno[1',2':4,5]imidazo[1,2-a]pyridine-8-carboxylic acid methyl ester, 2-(4-pyrrolidin-1-yl-phenyl)-imidazo[1,2-a]pyridine-6-carboxylic acid methyl ester, 2-(4-amino-phenyl)-imidazo[1,2-a]pyridine-6-carboxylic acid methyl ester, 2-(4-fluoro-phenyl)-imidazo[1,2-a]pyridine-6-carboxylic acid, 2-p-tolyl-imidazo[1,2-a]pyridine-6-carboxylic acid, 2-(4-diethylamino-phenyl)-imidazo[1,2-a]pyridine-6-carboxylic acid,
2-(4-fluoro-phenyl)-imidazo[1,2-a]pyridine-6-carboxylic acid tert-butylamide,
2-(4-fluoro-phenyl)-imidazo[1,2-a]pyridine-6-carboxylic acid amide,
2-(4-fluoro-phenyl)-imidazo[1,2-a]pyridine-6-carboxylic acid dimethylamide,
azetidin-1-yl-[2-(4-fluoro-phenyl)-imidazo[1,2-a]pyridin-6-yl]-methanone,
2-(4-fluoro-phenyl)-imidazo[1,2-a]pyridine-6-carbonitrile,
2-(4-diethylamino-phenyl)-imidazo[1,2-a]pyridine-6-carbonitrile,
2-p-tolyl-imidazo[1,2-a]pyridine-6-carbonitrile,
2-(3-chloro-phenyl)-imidazo[1,2-a]pyridine-6-carbonitrile,
2-(4-fluoro-phenyl)-N-hydroxy-imidazo[1,2-a]pyridine-6-carboxamidine,
N-hydroxy-2-p-tolyl-imidazo[1,2-a]pyridine-6-carboxamidine,
2-(4-diethylamino-phenyl)-N-hydroxy-imidazo[1,2-a]pyridine-6-carboxamidine,
2-(3-chloro-phenyl)-N-hydroxy-imidazo[1,2-a]pyridine-6-carboxamidine,
2-(4-fluoro-phenyl)-N-ethoxycarbonyloxy-imidazo[1,2-a]pyridine-6-carboxamidine,
6-bromo-2-(4-fluoro-phenyl)-imidazo[1,2-a]pyridine,
[4-(6-bromo-imidazo[1,2-a]pyridin-2-yl)-phenyl]-diethyl-amine,
2-(4-fluoro-phenyl)-6-nitro-imidazo[1,2-a]pyridine,
2-(4-fluoro-phenyl)-imidazo[1,2-a]pyridin-6-ylamine,
N-[2-(4-fluoro-phenyl)-imidazo[1,2-a]pyridin-6-yl]-formamide,
N-[2-(4-fluoro-phenyl)-imidazo[1,2-a]pyridin-6-yl]-acetamide,
3-[2-(4-fluoro-phenyl)-imidazo[1,2-a]pyridin-6-yl]-imidazolidine-2,4-dione,
3-[2-(4-fluoro-phenyl)-imidazo[1,2-a]pyridin-6-yl]-4H-1,2,4-oxadiazol-5-one, and
2-(4-fluoro-phenyl)-imidazo[1,2-a]pyridine-6-carboxamidine,
or a physiologically acceptable salt thereof.

4. A compound of formula Ib,

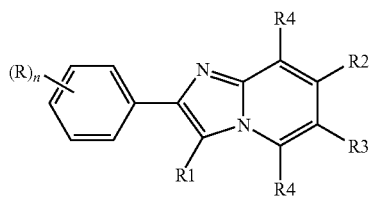

in which
R is chosen from F, Cl, $(C_1-C_6)$-alkyl which can be substituted by one or more fluorine atoms, $(C_1-C_6)$-alkoxy which can be substituted by one or more fluorine atoms, NR7R8, nitro and pentafluorosulfanyl;
or two adjacent R groups form, together with the carbon atoms which carry them, a 4-membered to 7-membered, partially unsaturated or aromatic heterocyclic ring which can be substituted by one or more identical or different substituents R13 and which can contain one or two ring members chosen from =N—, —N(R4)-, —C(=O)—,
—O—, —S—, —S(O)— and —S(O)$_2$— which can be identical or different, with the proviso that two ring members from the series —O—, —S—, —S(O)—, —S(O)$_2$— cannot be present in adjacent ring positions;
R1 is chosen from hydrogen and $(C_1-C_6)$-alkyl;
or R and R1 form together a $(C_1-C_2)$-alkylene or $(C_1-C_2)$-alkenylene chain if R is attached in ortho-position of the phenyl ring;
R2 is chosen from hydrogen, hydroxy and $(C_1-C_6)$-alkyl;
R3 is chosen from cyano, —C(=O)—NR9R10, amino, —N(R11)-C(=O)—R12 and —C(=NR5)-NHR6;
R4 is each time independently chosen from hydrogen and $(C_1-C_6)$-alkyl;
R5 is chosen from hydrogen, $(C_1-C_6)$-alkyl, $(C_1-C_6)$-alkylcarbonyl, $(C_1-C_6)$-alkoxycarbonyl, $(C_1-C_6)$-alkoxycarbonyloxy, $(C_1-C_{18})$-alkylcarbonyloxy-$(C_1-C_6)$-alkoxycarbonyl, $(C_6-C_{14})$-arylcarbonyl, $(C_6-C_{14})$-aryloxycarbonyl, hydroxy, $(C_1-C_6)$-alkylcarbonyloxy, $(C_6-C_{14})$-aryl-$(C_1-C_6)$-alkoxycarbonyl, $(C_1-C_6)$-alkylaminocarbonyloxy, di-($(C_1-C_6)$-alkyl)aminocarbonyloxy, $(C_1-C_6)$-alkylaminocarbonyl and di-($(C_1-C_6)$-alkyl)aminocarbonyl, wherein all aryl groups can be substituted by one or more identical or different substituents chosen from halogen, $(C_1-C_6)$-alkyl, $(C_1-C_6)$-alkoxy and trifluoromethyl;
R6 is chosen from hydrogen, cyano, hydroxy, $(C_1-C_6)$-alkoxy and $(C_6-C_{14})$-aryl-$(C_1-C_6)$ alkoxy;
or R5 and R6 form, together with the —N=C—NH— group which carries them, a 4-membered to 7-membered, partially unsaturated or aromatic heterocyclic ring which can be substituted by one or more identical or different substituents R14 and which, in addition to the nitrogen atoms being part of the —N=C—NH— group, can contain one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R7 and R8 are independently chosen from hydrogen and $(C_1-C_6)$-alkyl;
or R7 and R8 form, together with the nitrogen atom which carries them, a 4-membered to 7-membered, saturated, partially unsaturated or aromatic heterocyclic ring;
R9 and R10 are independently chosen from hydrogen and $(C_1-C_6)$-alkyl, with the proviso that at least one of R9 and R10 is not hydrogen;
or R9 and R10 form, together with the nitrogen atom which carries them, a 4-membered to 7-membered, saturated, partially unsaturated or aromatic heterocyclic ring;
R11 is hydrogen;
R12 is hydrogen;
or R11 and R12 form, together with the carbonylamino group which carries them, a 4-membered to 7-membered, saturated, partially unsaturated or aromatic heterocyclic ring which can be substituted by one or more identical or different substituents R15 and which, in addition to the carbonylamino group connecting R11 and R12, contains one or two further ring members chosen from =N—, —N(R4)-, —C(=O)—, —O—, —S—, —S(O)— and —S(O)$_2$— which can be identical or different, with the proviso that two ring members from the series —O—, —S—, —S(O)—, —S(O)$_2$— cannot be present in adjacent ring positions;
R13, R14 and R15 are independently chosen from halogen, $(C_1-C_6)$-alkyl, $(C_1-C_6)$-alkoxy and trifluoromethyl;

n is chosen from 1, 2, 3, 4 and 5;
or a physiologically acceptable salt thereof;
provided that 2-(4-amino-phenyl)-imidazo[1,2-a]pyridin-6-ylamine is excluded.

5. The compound as claimed in claim 4, in which in formula Ib
R is chosen from F, Cl, ($C_1$-$C_6$)-alkyl and NR7R8;
R1 is hydrogen;
R2 is hydrogen;
R3 is chosen from cyano, —C(=O)—NR9R10, amino, —N(R11)-C(=O)—R12 and —C(=NR5)-NHR6;
R4 is each time hydrogen;
R5 is chosen from hydrogen, ($C_1$-$C_6$)-alkoxycarbonyloxy and hydroxy;
R6 is hydrogen;
or R5 and R6 form, together with the —N=C—NH— group which carries them, a 4-membered to 7-membered, partially unsaturated or aromatic heterocyclic ring which, in addition to the nitrogen atoms being part of the —N=C—NH— group, can contain one or two further ring members chosen from —C(=O)— and —O—;
R7 and R8 are independently chosen from ($C_1$-$C_6$)-alkyl;
R9 and R10 are independently chosen from hydrogen and ($C_1$-$C_6$)-alkyl, with the proviso that at least one of R9 and R10 is not hydrogen;
or R9 and R10 form, together with the nitrogen atom which carries them, a 4-membered to 7-membered, saturated heterocyclic ring;
R11 is hydrogen;
R12 is hydrogen;
or R11 and R12 form, together with the carbonylamino group which carries them, a 4-membered to 7-membered, saturated heterocyclic ring which, in addition to the carbonylamino group connecting R11 and R12, contains one or two further ring members chosen from —N(R4)- and —C(=O)—;
n is 1;
or a physiologically acceptable salt thereof;
provided that 2-(4-amino-phenyl)-imidazo[1,2-a]pyridin-6-ylamine is excluded.

6. The compound as claimed in claim 4, which is chosen from:
2-(4-bromo-phenyl)-3-methyl-imidazo[1,2-a]pyridine-6-carboxylic acid methyl ester,
3-methyl-2-phenyl-imidazo[1,2-a]pyridine-6-carboxylic acid methyl ester,
2-(2-oxo-1,2,3,4-tetrahydro-quinolin-6-yl)-imidazo[1,2-a]pyridine-6-carboxylic acid methyl ester,
2-(2-fluoro-phenyl)-imidazo[1,2-a]pyridine-6-carboxylic acid methyl ester,
2-pentafluoro-phenyl-imidazo[1,2-a]pyridine-6-carboxylic acid methyl ester,
2-p-tolyl-imidazo[1,2-a]pyridine-6-carboxylic acid methyl ester,
2-naphthalen-2-yl-imidazo[1,2-a]pyridine-6-carboxylic acid methyl ester,
2-(3-fluoro-phenyl)-imidazo[1,2-a]pyridine-6-carboxylic acid methyl ester,
2-(4-trifluoromethyl-phenyl)-imidazo[1,2-a]pyridine-6-carboxylic acid methyl ester,
2-(4-trifluoromethoxy-phenyl)-imidazo[1,2-a]pyridine-6-carboxylic acid methyl ester,
2-(4-diethylamino-phenyl)-imidazo[1,2-a]pyridine-6-carboxylic acid methyl ester,
2-(4-cyano-phenyl)-imidazo[1,2-a]pyridine-6-carboxylic acid methyl ester,
2-(2-chloro-phenyl)-imidazo[1,2-a]pyridine-6-carboxylic acid methyl ester,
2-(4-bromo-3-sulfamoyl-phenyl)-imidazo[1,2-a]pyridine-6-carboxylic acid methyl ester,
2-(4-fluoro-3-sulfamoyl-phenyl)-imidazo[1,2-a]pyridine-6-carboxylic acid methyl ester,
2-(3-cyano-phenyl)-imidazo[1,2-a]pyridine-6-carboxylic acid methyl ester,
2-(3-bromo-phenyl)-imidazo[1,2-a]pyridine-6-carboxylic acid methyl ester,
2-(2,4-dimethyl-phenyl)-imidazo[1,2-a]pyridine-6-carboxylic acid methyl ester,
2-(3,4-dichloro-phenyl)-imidazo[1,2-a]pyridine-6-carboxylic acid methyl ester,
2-(4-chloro-3-methyl-phenyl)-imidazo[1,2-a]pyridine-6-carboxylic acid methyl ester,
2-(2,4-dichloro-phenyl)-imidazo[1,2-a]pyridine-6-carboxylic acid methyl ester,
2-(3-chloro-phenyl)-imidazo[1,2-a]pyridine-6-carboxylic acid methyl ester,
2-(3,5-difluoro-phenyl)-imidazo[1,2-a]pyridine-6-carboxylic acid methyl ester,
2-(3-trifluoromethyl-phenyl)-imidazo[1,2-a]pyridine-6-carboxylic acid methyl ester,
2-(2,3-dihydro-benzo[1,4]dioxin-6-yl)-imidazo[1,2-a]pyridine-6-carboxylic acid methyl ester,
2-(2,6-dichloro-4-trifluoromethyl-phenyl)-imidazo[1,2-a]pyridine-6-carboxylic acid methyl ester,
2-(2-nitro-phenyl)-imidazo[1,2-a]pyridine-6-carboxylic acid methyl ester,
2-biphenyl-4-yl-imidazo[1,2-a]pyridine-6-carboxylic acid methyl ester,
2-(4-nitro-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(4-sulfamoyl-phenyl)-imidazo[1,2-a]pyridine-6-carboxylic acid methyl ester,
2-(2-trifluoromethyl-phenyl)-imidazo[1,2-a]pyridine-6-carboxylic acid methyl ester,
11H-indeno[1',2':4,5]imidazo[1,2-a]pyridine-8-carboxylic acid methyl ester,
2-(4-pyrrolidin-1-yl-phenyl)-imidazo[1,2-a]pyridine-6-carboxylic acid methyl ester,
2-p-tolyl-imidazo[1,2-a]pyridine-6-carboxylic acid,
2-(4-diethylamino-phenyl)-imidazo[1,2-a]pyridine-6-carboxylic acid,
2-(4-fluoro-phenyl)-imidazo[1,2-a]pyridine-6-carboxylic acid tert-butylamide,
2-(4-fluoro-phenyl)-imidazo[1,2-a]pyridine-6-carboxylic acid dimethylamide,
azetidin-1-yl-[2-(4-fluoro-phenyl)-imidazo[1,2-a]pyridin-6-yl]-methanone,
2-(4-fluoro-phenyl)-imidazo[1,2-a]pyridine-6-carbonitrile,
2-(4-diethylamino-phenyl)-imidazo[1,2-a]pyridine-6-carbonitrile,
2-p-tolyl-imidazo[1,2-a]pyridine-6-carbonitrile,
2-(3-chloro-phenyl)-imidazo[1,2-a]pyridine-6-carbonitrile,
2-(4-fluoro-phenyl)-N-hydroxy-imidazo[1,2-a]pyridine-6-carboxamidine,
N-hydroxy-2-p-tolyl-imidazo[1,2-a]pyridine-6-carboxamidine,
2-(4-diethylamino-phenyl)-N-hydroxy-imidazo[1,2-a]pyridine-6-carboxamidine, 2-(3-chloro-phenyl)-N-hydroxy-imidazo[1,2-a]pyridine-6-carboxamidine,
2-(4-fluoro-phenyl)-N-ethoxycarbonyloxy-imidazo[1,2-a]pyridine-6-carboxamidine,
6-bromo-2-(4-fluoro-phenyl)-imidazo[1,2-a]pyridine,
[4-(6-bromo-imidazo[1,2-a]pyridin-2-yl)-phenyl]-diethyl-amine,
2-(4-fluoro-phenyl)-imidazo[1,2-a]pyridin-6-ylamine,
N-[2-(4-fluoro-phenyl)-imidazo[1,2-a]pyridin-6-yl]-formamide,
3-[2-(4-fluoro-phenyl)-imidazo[1,2-a]pyridin-6-yl]-imidazolidine-2,4-dione,
3-[2-(4-fluoro-phenyl)-imidazo[1,2-a]pyridin-6-yl]-4H-1,2,4-oxadiazol-5-one, and
2-(4-fluoro-phenyl)-imidazo[1,2-a]pyridine-6-carboxamidine,
or a physiologically acceptable salt thereof.

7. A pharmaceutical composition comprising at least one compound as claimed in claim 4, or a physiologically acceptable salt thereof, and a pharmaceutically acceptable carrier.

* * * * *